United States Patent
Castano Mansanet et al.

(10) Patent No.: US 7,393,868 B2
(45) Date of Patent: Jul. 1, 2008

(54) AMPA RECEPTOR POTENTIATORS

(75) Inventors: Ana Maria Castano Mansanet, Madrid (ES); Frederic Laurent Cordier, Madrid (ES); Esteban Dominguez-Manzanares, Madrid (ES); Jian Eric Hong, Foster City, CA (US); William Joseph Hornback, Fishers, IN (US); Delu Jiang, Westfield, IN (US)

(73) Assignee: Eli Lilly and Company, Indianpolis, IN (US)

( * ) Notice: Subject to any disclaimer, the term of this patent is extended or adjusted under 35 U.S.C. 154(b) by 190 days.

(21) Appl. No.: 11/446,840

(22) Filed: Jun. 5, 2006

(65) Prior Publication Data

US 2007/0142441 A1   Jun. 21, 2007

Related U.S. Application Data

(60) Provisional application No. 60/724,206, filed on Oct. 6, 2005.

(30) Foreign Application Priority Data

Jun. 6, 2005 (EP) ................. 05380117
Aug. 18, 2005 (EP) ................. 05380187

(51) Int. Cl.
*A61K 31/381* (2006.01)
*A61K 31/4155* (2006.01)
*A61K 31/4418* (2006.01)
*C07D 213/61* (2006.01)
*C07D 231/16* (2006.01)

(52) U.S. Cl. .......... 514/352; 514/403; 514/447; 546/305; 548/372.1; 549/63

(58) Field of Classification Search ........ 514/352, 514/403, 447; 546/305; 548/372.1; 549/63
See application file for complete search history.

(56) References Cited

U.S. PATENT DOCUMENTS

2004/0087604 A1   5/2004   Tsuri et al.

FOREIGN PATENT DOCUMENTS

| WO | WO 98/33496 | 8/1998 |
|----|----|----|
| WO | WO 00/06083 | 2/2000 |
| WO | WO 01/42203 A1 | 6/2001 |
| WO | WO 02/32858 A1 | 4/2002 |
| WO | WO 02/098847 A1 | 12/2002 |
| WO | WO 02/100851 A2 | 12/2002 |
| WO | WO 03/010158 A1 | 2/2003 |
| WO | WO 2005/070916 A1 | 8/2005 |
| WO | WO 2006/015827 A1 | 2/2006 |

OTHER PUBLICATIONS

Ornstein et al., "Biarylproplsulfonamides as Novel, Potent Potentiators of 2-Amino-3-(5-methyl-3-hydroxyisoxazol-4-yl)-propanoic Acid (AMPA) Receptors," *J. Med. Chem.*, vol. 43, pp. 4354-4358 (2000).

*Primary Examiner*—Taofiq Solola
(74) *Attorney, Agent, or Firm*—Tonya L. Combs

(57) ABSTRACT

The present invention relates to AMPA receptor potentiators of Formula I:

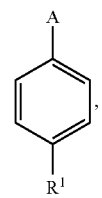

formulations comprising them, methods for their use, and intermediates useful for their preparation.

7 Claims, No Drawings

AMPA RECEPTOR POTENTIATORS

CROSS REFERENCE TO RELATED APPLICATIONS

This patent application claims the benefit of priority under Title 35 United States Code, section 119(e), of EP Provisional Patent Application Number 05380117.1, Filed Jun. 6, 2005, EP Provisional Patent Application Number 05380187.4, filed Aug. 18, 2005 and U.S. Provisional Patent Application No. 60/724,206 filed Oct. 6, 2005.

BACKGROUND OF THE INVENTION

Glutamate is the major excitatory neurotransmitter in the central nervous system. Three glutamate receptor ion channel subtypes have been identified based on their sensitivity to the selective activators (agonists) N-methyl-D-aspartate (NMDA), α-amino-3-hydroxy-5-methyl-4-isoxazole propionic acid (AMPA), and kainate.

AMPA receptors mediate cellular responses to glutamate by direct and indirect mechanisms. When activated by glutamate or AMPA, AMPA receptor ion channels allow sodium ions ($Na^+$) and calcium ions ($Ca^{2+}$) to pass directly through the channel pore. In addition, AMPA receptor ion channels can facilitate the activation of NMDA receptors by initiating cellular depolarization that relieves magnesium ion ($Mg^{2+}$)-dependent block of NMDA receptors.

Multiple AMPA receptor subtypes have been identified and cloned: GluR1, GluR2, GluR3, and GluR4 as disclosed by Hollmann and Heinemann, *Ann. Rev. Neurosci.,* 17, 31-108 (1994). Each subunit consists of a sequence of approximately 900 amino acids. Four subunits are thought to assemble to form a tetrameric ion channel complex with the functional properties of this ion channel most likely being determined by its subunit composition.

Ion channel currents activated by glutamate via AMPA receptors are transient. The time course of currents is modified by refractory states caused during glutamate binding which is referred to as desensitization and by the rate of glutamate removal from the ion channel binding site which results in deactivation. Ion influx through AMPA receptors may be enhanced by compounds that either prevent desensitization or by compounds that slow deactivation rates. Compounds that enhance glutamate-stimulated ion influx at AMPA receptors are known as positive AMPA receptor allosteric modulators or AMPA receptor potentiators. One such compound, which selectively potentiates AMPA receptor function, is cyclothiazide. Since AMPA receptors play a pivotal role in mediating fast excitatory transmission in the central nervous system, molecules that enhance AMPA receptor function have multiple therapeutic targets.

Compounds that allosterically potentiate AMPA receptors have been shown to enhance synaptic activity in vitro and in vivo as disclosed, for example, by I. Ito, et al., *J. Physiol.,* 424, 533-543 (1990) and A. Copani, et al., *Journal of Neurochemistry,* 58, 1199-1204(1992). Such compounds have also been shown to enhance learning and memory in rats, monkeys, and humans, and are reviewed by Gouliaev and Senning, *Brain Research Reviews,* 19, 180-222 (1994).

International Patent Application Publication WO 98/33496 published Aug. 6, 1998 discloses certain sulfonamide derivatives which are useful, for example, for treating psychiatric and neurological disorders, for example cognitive disorders, Alzheimer's disease, age-related dementias, age-induced memory impairment, tardive dyskinesia, Huntington's chorea, myoclonus, Parkinson's disease, reversal of drug-induced states (such as cocaine, amphetamines, alcohol-induced states), depression, attention deficit disorder, attention deficit hyperactivity disorder, psychosis, cognitive deficits associated with psychosis, and drug-induced psychosis. P. L. Ornstein, et al. *J. Med. Chem.,* 43, 4354(2000) further disclose biarylpropylsulfonamides which are potent potentiators of AMPA receptors. In addition, X. Li, et al., *Neuropharmacology,* 40, 1028 (2001) disclose antidepressant-like actions of an AMPA receptor potentiators. D. D. Schoepp, et al. and Tizzano, et al., *Society for Neuroscience Abstracts,* 26(1-2), 528.19 and 528.20, 30th Annual Meeting, New Orleans, (Nov. 4-9, 2000) disclose an orally active AMPA receptor potentiator that enhances spatial learning and memory performance in rats, and reverses both pharmacologically and age-associated learning and memory deficit in rats. New AMPA receptor potentiators are needed to treat these neurological disorders.

SUMMARY OF THE INVENTION

The present invention provides compounds of Formula I:

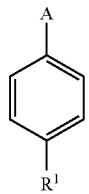

where:
A is selected from the group consisting of

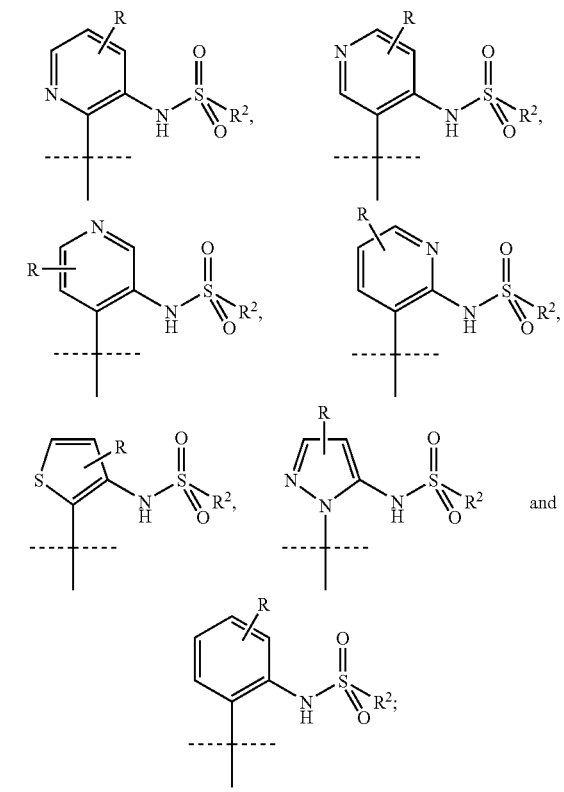

R is H, halo, —COOH, or —CH$_2$COOH;

R$^1$ is phenyl optionally substituted with a first substituent selected from the group consisting of halo, cyano, $C_1$-$C_4$ acyl, —COOH, —NHR$^3$, $C_1$-$C_2$ alkyl substituted with —NHCH$_3$, —N(SO$_2$($C_1$-$C_3$ alkyl))$_2$, —COOH, —CONH$_2$, cyano, hydroxy, or tetrazol-5-yl, —OCH$_2$COOH, —SCH$_2$COOH, —C(O)CH$_2$CH$_2$COOH, —SO$_2$NH$_2$, tetrazol-5-yl, and 1,2,4-triazol-1-yl; optionally further substituted with a second substituent selected from the group consisting of: halo, trifluoromethyl, cyano, nitro, C$_1$-C$_4$ alkoxy, hydroxy, C$_1$-C$_4$ alkyl, C$_1$-C$_4$ alkylthio, —NHCH$_2$CN, —OCH$_2$CN, —NHSO$_2$CH(CH$_3$)$_2$, and —C(O)NHR$^4$; optionally further substituted with a third substituent selected from the group consisting of halo and cyano; optionally further substituted with a fourth substituent selected from the group consisting of halo;

R$^2$ is C$_1$-C$_4$ alkyl or dimethylamino;

R$^3$ is —SO$_2$(C$_1$-C$_3$ alkyl), C$_1$-C$_4$ acyl, C$_1$-C$_4$ alkyl, or hydrogen;

R$^4$ is hydrogen, C$_1$-C$_4$ alkyl, or —SO$_2$(C$_1$-C$_4$ alkyl); or a pharmaceutically acceptable salt thereof, provided that when A is

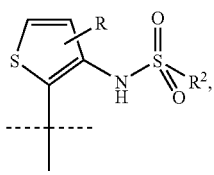

R is H, and R$^2$ is isopropyl, then R$^1$ is not 2-ethoxy-4-carboxyphenyl.

The present invention also provides intermediates of Formula II:

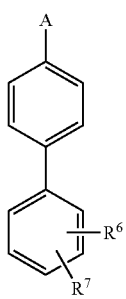

II where:

A is selected from the group consisting of

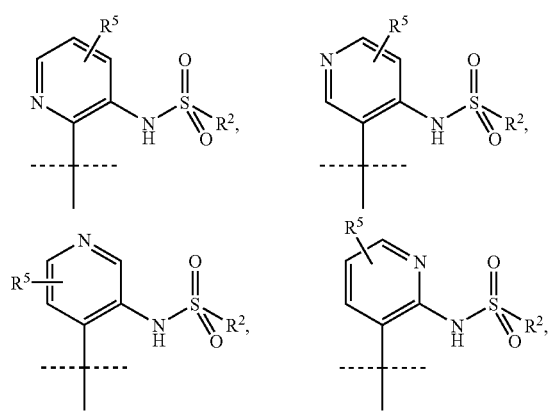

-continued

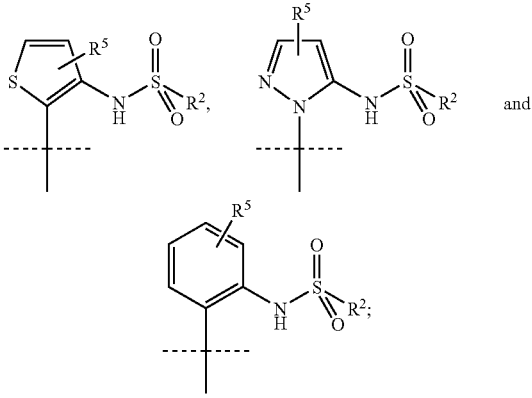

R$^2$ is C$_1$-C$_4$ alkyl or dimethylamino;

R$^5$ is H, halo, —COOR$^8$, or —CH$_2$COOR$^8$;

R$^6$ is H, cyano, C$_1$-C$_4$ alkoxy, halo, hydroxy, trifluoromethyl, or methylthio;

R$^7$ is —COOR$^9$, —C(O)CH$_2$CH$_2$COOR$^9$, —OCH$_2$COOR$^9$, —SCH$_2$COOR$^9$, or C$_1$-C$_2$ alkyl substituted with —COOR$^9$;

R$^8$ and R$^9$ are each independently selected from the group consisting of hydrogen and C$_1$-C$_4$ alkyl provided that at least one of R$^8$ and R$^9$ is other than hydrogen; or a base addition salt thereof.

The present invention provides a compound of Formula I for use as a pharmaceutical. The present invention further provides a method of potentiating glutamate receptor function in a patient, which comprises administering to said patient in need of such treatment an effective amount of a compound of Formula I or a pharmaceutically acceptable salt thereof.

In addition, the present invention further provides a method of treating schizophrenia, cognitive deficits associated with schizophrenia, Alzheimer's disease, dementia of the Alzheimer's type, mild cognitive impairment, Parkinson's disease, or depression in a patient, which comprises administering to a patient in need of such treatment an effective amount of a compound of Formula I or a pharmaceutically acceptable salt thereof.

According to another aspect, the present invention provides the use of a compound of Formula I, or a pharmaceutically acceptable salt thereof, for the manufacture of a medicament for treating schizophrenia, cognitive deficits associated with schizophrenia, Alzheimer's disease, dementia of the Alzheimer's type, mild cognitive impairment, Parkinson's disease, or depression.

In addition, the present invention provides the use of a compound of Formula I, or a pharmaceutically acceptable salt thereof, for treating schizophrenia, cognitive deficits associated with schizophrenia, Alzheimer's disease, dementia of the Alzheimer's type, mild cognitive impairment, Parkinson's disease, or depression.

The invention further provides pharmaceutical compositions comprising, a compound of Formula I, or a pharmaceutically acceptable salt thereof, and a pharmaceutically acceptable carrier, diluent, or excipient.

Additionally, the use of compounds of Formula I in conjunction with antipsychotics, antidepressants, and drugs useful in treating cognitive disorder are contemplated within the scope of the present invention. WO 2005/040110, teaches the use of compounds that potentiate glutamate receptor function in conjunction with antipsychotics, antidepressants and drugs useful in treating cognitive disorder.

DETAILED DESCRIPTION OF THE INVENTION

As used herein the term "potentiating glutamate receptor function" refers to. any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by compounds of Formula I and their pharmaceutically acceptable salts through their action as potentiators of glutamate receptor function. Such conditions include those associated with glutamate hypofunction, such as psychiatric and neurological disorders, for example cognitive disorders and neuro-degenerative disorders such as Alzheimer's disease; dementia of the Alzheimer's type, age-related dementias; age-induced memory impairment; cognitive deficits due to autism, Down's syndrome and other central nervous system disorders with childhood onset, cognitive deficits post electroconvulsive therapy, movement disorders such as tardive dyskinesia, Huntington's chorea, myoclonus, dystonia, spasticity, Parkinson's disease; reversal of drug-induced states (such as cocaine, amphetamines, alcohol-induced states); depression; attention deficit disorder; attention deficit hyperactivity disorder; psychosis such as schizophrenia; cognitive deficits associated with psychosis such as schizophrenia, drug-induced psychosis, stroke, and sexual dysfunction. Compounds of Formula I may also be useful for improving memory (both short term and long term) and learning ability. The present invention provides the use of compounds of Formula I for the treatment of each of these conditions.

It is understood by one of ordinary skill in the art that cognition includes various "domains". These domains include short-term memory, long term memory, working memory, executive function, and attention. As used herein the term "cognitive disorder" is meant to encompass any disorder characterized by a deficit in one or more of the cognitive domains, including but not limited to short term memory, long term memory, working memory, executive function, and attention. It is further understood that the term "cognitive disorder" includes, but is not limited to the following specific disorders: age-related cognitive decline, mild cognitive impairment, Alzheimer's disease, dementia, dementia of the Alzheimer's type, Parkinson's dementia, Lewy Body dementia, substance-induced persisting dementia, alcohol-induced persisting dementia, alcohol-induced cognitive impairment, AIDS-induced dementia, learning disorders, cognitive deficits subsequent to cardiac bypass surgery and grafting, stroke, cerebral ischemia, spinal cord trauma, head trauma, perinatal hypoxia, cardiac arrest, and hypoglycemic neuronal damage, vascular dementia, multi-infarct dementia, cognitive deficits associated with amylotrophic lateral sclerosis, and cognitive deficits associated with multiple sclerosis. Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405(2001); Petersen, et al., *Arch. Neurol.*, 56, 303-308 (1999)).

The fourth edition of the Diagnostic and Statistical Manual of Mental Disorders (DSM-IV) (1994, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the International Statistical Classification of Diseases and Related Health Problems, tenth revision (ICD-10) (1992, World Health Organization, Geneva) and that terminology and classification systems evolve with medical scientific progress.

The present invention includes the pharmaceutically acceptable salts of the compounds defined by Formula I. A compound of this invention can possess a sufficiently acidic group, and accordingly react with any of a number of organic and inorganic bases to form a pharmaceutically acceptable salt. The term "pharmaceutically acceptable salt" as used herein, refers to salts of the compounds of Formula I which are substantially non-toxic to living organisms. Typical pharmaceutically acceptable salts include those salts prepared by reaction of the compounds of the present invention with a pharmaceutically acceptable organic or inorganic base. Such salts are known as base addition salts. Such salts include the pharmaceutically acceptable salts listed in *Journal of Pharmaceutical Science*, 66, 2-19 (1977), which are known to the skilled artisan. Magnesium, diethylamine, hemipiperazine, and tert-butylamine salts are preferred. The tert-butylamine salts are most preferred.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention. The specific stereoisomers and enantiomers of compounds of Formula I can be prepared by one of ordinary skill in the art utilizing well known techniques and processes, such as those disclosed by J. Jacques, et al., "*Enantiomers Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

As used herein, the terms "Halo", "Halide" or "Hal" refers to a chlorine, bromine, iodine or fluorine atom, unless otherwise specified herein.

As used herein the term "$C_1$-$C_4$ alkyl" refers to a straight or branched, monovalent, saturated aliphatic chain of one to four carbon atoms and includes, but is not limited to, methyl, ethyl, propyl, isopropyl, butyl, isobutyl, and t-butyl. The term "$C_1$-$C_4$ alkyl" includes within its definition the term "$C_1$-$C_3$ alkyl".

As used herein the term "$C_1$-$C_4$ alkoxy" refers to a straight or branched alkyl chain having from one to four carbon atoms attached to an oxygen atom. Typical $C_1$-$C_4$ alkoxy groups include methoxy, ethoxy, propoxy, isopropoxy, butoxy, tert-butoxy and the like. The term "$C_1$-$C_4$ alkoxy" includes within its definition the term "$C_1$-$C_3$ alkoxy".

As used herein the term "$C_1$-$C_4$ acyl" refers to a straight or branched alkyl chain having from one to three carbon atoms attached to a carbonyl group. Examples include, but are not limited to acetyl, propionyl, butyryl, 2-methylpropionyl and the like. The term "$C_1$-$C_4$ acyl" includes within its definition the term "$C_1$-$C_3$ acyl".

As used herein the term "$C_1$-$C_4$ alkylthio" refers to a straight or branched alkyl chain having from one to four carbon atoms attached to an sulfur atom. Typical $C_1$-$C_4$ alkylthio groups include methylthio, ethylthio, propylthio, isopropylthio, butylthio, tert-butylthio and the like. The term "$C_1$-$C_4$ alkylthio" includes within its definition the term "$C_1$-$C_3$ alkythio".

An further embodiment of the present invention is compounds of Formula I where A is selected from the group consisting of:

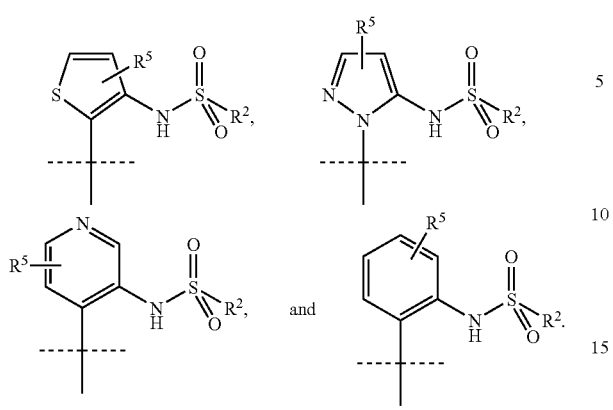

Certain classes of compounds of Formula I are preferred AMPA potentiaters. The following paragraphs describe such preferred classes:

a) A is

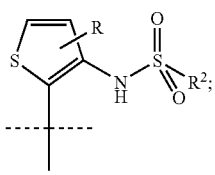

b) R is hydrogen;
c) $R^1$ is phenyl substituted with a single substituent;
d) $R^1$ is phenyl substituted with a single substituent selected from the group consisting of cyano, tetrazol-5-yl, $C_1$-$C_2$ alkyl substituted with —COOH or tetrazol-5-yl, —SO$_2$NH$_2$, —OCH$_2$COOH, and —SCH$_2$COOH;
e) $R^1$ is phenyl mono-substituted in the 4-position with a substituent selected from the group consisting of tetrazol-5-yl, —OCH$_2$COOH, —SCH$_2$COOH, and $C_1$-$C_2$ alkyl substituted with —COOH, in the 3-position with a substituent selected from the group consisting of —SONH$_2$ and $C_1$-$C_2$ alkyl substituted with tetrazol-5-yl, or in the 2-position with cyano;
f) $R^1$ is phenyl substituted with two substituents;
g) $R^1$ is phenyl substituted with a first substituent selected from the group consisting of $C_1$-$C_4$ alkoxy, hydroxy, halo, cyano, —COOH, and —NHSO$_2$CH(CH$_3$)$_2$, and with a second substituent selected from the group consisting of amino, trifluoromethyl, —COOH, —C(O)NHR$^3$, tetrazol-5-yl, —OCH$_2$COOH, and $C_1$-$C_2$ alkyl substituted with —COOH, provided that when A is

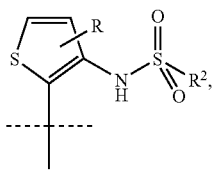

R is H, and $R^2$ is isopropyl, then $R^1$ is not 2-ethoxy-4-carboxyphenyl;

h) $R^1$ is phenyl substituted in the 2-position with a substituent selected from the group consisting of $C_1$-$C_4$ alkoxy, hydroxy, halo, cyano, —COOH, and —NHSO$_2$CH(CH$_3$)$_2$, and further substituted in the 4-position with tetrazol-5-yl, —COOH, —C(O)NHR$^3$, or $C_1$-$C_2$ alkyl substituted with —COOH, in the 5-position with amino, —COOH, or —OCH$_2$COOH, or in the 6-position with —COOH, provided that when A is

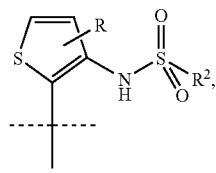

R is H, and $R^2$ is isopropyl, then $R^1$ is not 2-ethoxy-4-carboxyphenyl;

i) $R^1$ is 2-cyano-3-fluoro-4-hydroxy-5-fluorophenyl;
j) $R^1$ is 2-cyano-4-carboxyphenyl;
k) $R^2$ is $C_1$-$C_4$ alkyl;
l) $R^2$ is isopropyl;
m) The compound of Formula I is a free acid;
n) The compound of Formula I is a salt;
o) The compound of Formula I is a hydrate;
p) The compound of Formula I is an anhydrate;
q) The compound of Formula I is the hemipiperazine salt;
r) The compound of Formula I is the diethylamine salt;
s) The compound of Formula I is the tert-butylamine salt.

Preferred embodiments of the invention include all combinations of paragraphs a)-s). Especially preferred compounds of Formula I are those where A is

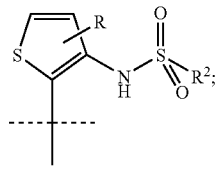

R is hydrogen; $R^1$ is as described in paragraph h); and $R^2$ is $C_1$-$C_4$ alkyl. It is also preferred that A is

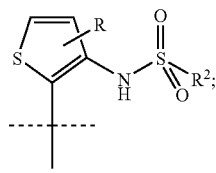

R is hydrogen; $R^1$ is as described in paragraph h); and $R^2$ is isopropyl. It is particularly preferred that A is

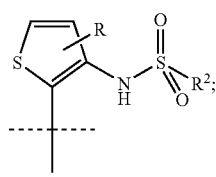

R is hydrogen; $R^1$ is phenyl substituted in the 2-position with cyano and in the 4-position with —COOH; and $R^2$ is isopropyl. It is most preferred that A is

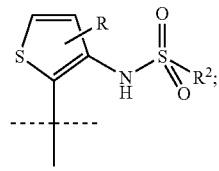

R is hydrogen; $R^1$ is 2-cyano-4-carboxyphenyl; and $R^2$ is isopropyl.

Although all of the intermediates of Formula II are useful for preparing compounds of the present invention, certain classes are preferred:

t) A is

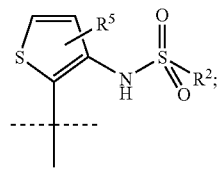

u) $R^2$ is $C_1$-$C_4$ alkyl;
v) $R^2$ is isopropyl;
w) $R^5$ is hydrogen;
x) $R^6$ is in the 2-position of the phenyl ring to which it is attached;
y) $R^6$ is in the 2-position of the phenyl ring to which it is attached and is selected from the group consisting of hydrogen, cyano, and $C_1$-$C_4$ alkoxy;
z) $R^9$ is $C_1$-$C_4$ alkyl.

Especially preferred compounds of Formula II are those where A is

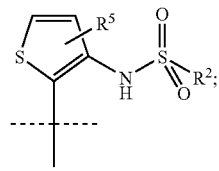

$R^5$ is hydrogen; $R^2$ is $C_1$-$C_4$ alkyl; $R^6$ is in the 2-position of the phenyl to which it is attached and is selected from the group consisting of cyano and $C_1$-$C_4$ alkoxy; $R^7$ is in the 4-position of the phenyl ring to which it is attached and is —COOR$^9$, and $R^9$ is $C_1$-$C_4$ alkyl. It is also preferred that A is

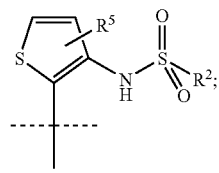

$R^5$ is hydrogen; $R^2$ is isopropyl; $R^6$ is in the 2-position of the phenyl to which it is attached and is selected from the group consisting of cyano and $C_1$-$C_4$ alkoxy; $R^7$ is in the 4-position of the phenyl ring to which it is attached and is —COOR$^9$, and $R^9$ is $C_1$-$C_4$ alkyl. It is most preferred that A is

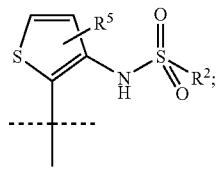

$R^5$ is hydrogen; $R^2$ is isopropyl; $R^6$ is in the 2-position of the phenyl to which it is attached and is selected from the group consisting of cyano, methoxy, and ethoxy; $R^7$ is in the 4-position of the phenyl ring to which it is attached and is —COOR$^9$, and $R^9$ is methyl or ethyl.

The compounds of Formula I can be prepared by one of ordinary skill in the art following art recognized techniques and procedures. More specifically, compounds of Formula I can be prepared as set forth in the schemes, methods, and examples set forth below. The reagents and starting materials are readily available to one of ordinary skill in the art. All substituents, unless otherwise specified, are as previously defined.

The compounds of Formula I where A and $R^1$ are as previously defined may be prepared as illustrated in the following scheme where (i) is a suitable aryl boronic acid, aryl trimethylstannyl, or aryl boronoic ester, and X is bromo, iodo, chloro, or trifluoromethane-sulfoxy.

Scheme I

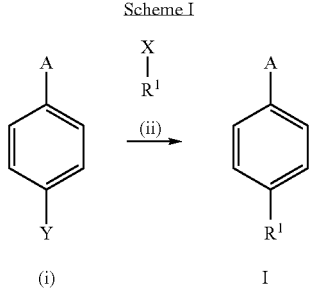

The compound of structure (ii) is coupled to a suitable phenyl boronic acid, suitable phenyl boronic ester, or suitable phenyl trimethylstannane (i), under Suzuki-Type or Stille-Type coupling reaction conditions well known to one of ordinary skill in the art to provide the compound of Formula I. See Suzuki, A., *Journal of Organometallic Chemistry*, 576, 147-168 (1999), and Miyaura and Suzuki, *Chemical Reviews*, 95, 2457-2483 (1995) for examples of general cross-coupling techniques and for methods for preparing suitable starting materials and reagents.

More specifically, the compound of structure (ii) is combined with about 1.0 to 1.5 equivalents of the suitable phenyl boronic acid or ester (i) in a suitable organic solvent or a suitable mixture of solvents. Examples of suitable organic solvents include 1,4-dioxane, dimethoxyethane (DME), DMF, benzene, toluene, acetone, ethanol (EtOH), and the like. Examples of suitable solvent mixtures include DME/EtOH, THF:Water, and the like. A suitable catalyst, such as tetrakis(triphenylphosphine)palladium, dichlorobis(triphenylphosphine)-palladium (II), Pd(PCy$_3$)$_2$Cl$_2$, or [1,1-bis(diphenylphospino)ferrocene] dichloro-palladium(II) or palladium black and a suitable base, for example sodium carbonate, are added to the reaction mixture with stirring.

Alternatively, the skilled artisan appreciates that compounds of Formula (I) may also be prepared by coupling a suitable aryl halide with a suitable aryl boronic acid, suitable aryl boronic ester, or suitable aryl trimethylstannyl compound under Suzuki-Type or Stille-Type coupling reaction conditions well known to one of ordinary skill in the art to provide the compound of Formula (I).

The requisite boronic acids and esters can be prepared as illustrated in the following scheme where A is as previously defined, and Hal is bromo or iodo.

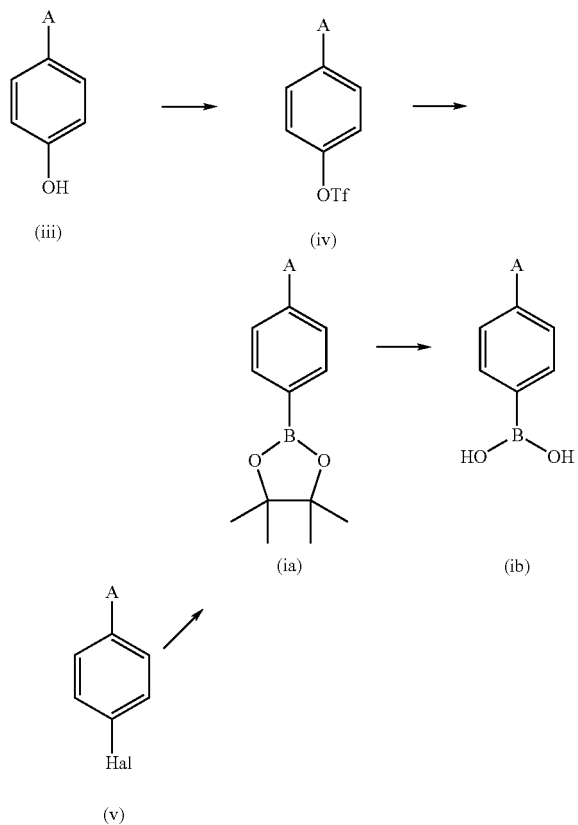

An appropriately substituted phenol (iii) is reacted with a triflating reagent, such as triflic anhydride or N-phenyltrifluoromethanesulphonimide, in the presence of base, for example DMAP or sodium hydroxide in a suitable solvent, such as methylene chloride or tetrahydrofuran to give the triflate (iv). The resulting triflate is dissolved in a suitable solvent such as acetonitrile or dimethylsulfoxide and reacted in the presence of a base such as triethylamine or potassium acetate, catalyst such as [1,1'-bis(disphenylphosphino)-ferrocene]dichloropalladium(II) complex, and a borane such as bis(pinacolato)borane to form the requisite boronic ester (ia). Alternatively, PdCl$_2$ (dppf) and the base potassium acetate in dimethylformamide may be employed if necessary or desired. The boronic acid ester may also be prepared by reacting the phenyl halide (v) in an appropriate solvent such as acetonitrile or dimethylsulfoxide and a base such as triethylamine or potassium acetate is added. A catalyst such as [1,1'-bis(disphenylphosphino)-ferrocene]dichloropalladium (II) complex and a borane such as bis(pinacolato)borane are added. The skilled artisian appreciates that the resultant borate ester can be hydrolyzed under conditions well known in the art, with an acid such as hydrochloride acid or in a suitable solvent such as acetone and in the presence of an oxidizing agent such as sodium periodate and an ammonium acetate solution to provide the boronic acid (ib).

The requisite phenyl halides (v) may be prepared as shown in Scheme III, wherein A is as previously defined.

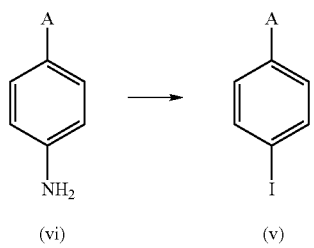

The aniline (vi) is reacted with a suitable oxidizing reagent, such as isoamyl nitrite in a suitable solvent, such as acetonitrile, in the presence of a source of halide, such as diiodomethane, to provide compounds of formula (v).

Certain compounds of Fomula I may be serve as intermediates to further compounds of Formula I via reactions and functional group transformations familiar to those skilled in the art. See Larock, R., "*Organic Transformations,*" VCH Publishing, Inc., New York, 1989. For example, an amino group is reacted with a suitable sulfonyl chloride in the presence of pyridine or aqueous base, such as triethylamine, under conditions well known in the art to provide the corresponding sulfonamide. Furthermore, nitro substitutents are readily converted to amines by reacting the nitro-containing compound with a suitable reducing agent, such as tin chloride, in an appropriate solvent, for example, ethanol. In addition, carboxylic esters of Formula II are converted to carboxylic acids of Formula I under conditions well known to the skilled artisan, for example by treating an ester of Formula II in a suitable solvent or solvent mixture such as THF, methanol, ethanol, and the like with water and a slight excess of suitable base, such as lithium hydroxide, sodium hydroxide, potassium hydroxide and the like. The resultant carboxylic acid can then be converted to the primary amide under well known conditions. For example, the carboxylic acid compound of Formula I is dissolved in a suitable organic solvent, such as methylene chloride or THF and treated with oxalyl chloride optionally followed by addition of a catalytic amount of DMF with stirring. The reaction mixture is stirred and concentrated then dissolved in a suitable organic solvent, such as methylene chloride or THF, and treated with a slight excess of an ammonia hydroxide or ammonia/methanol or ammonia/dioxane solution with stirring. Primary amide compounds of Formula I can be converted to tetrazolyl compounds of Formula I under standard conditions. For example, the primary amide compound of Formula I is reacted with silicon tetrachloride and sodium azide in the presence of a suitable organic solvent, such as acetonitrile. Alternatively, tetrazolyl compounds Formula I are formed by reacting a cyano compound of Formula I with sodium azide and triethylamine in a suitable organic solvent.

The examples set forth herein represent typical syntheses of the compounds of the present invention. The reagents and starting materials are readily available to one of ordinary skill in the art. Nomenclature for examples set forth herein with AutoNom 2000 Add-in for MDL® ISIS/Desktop. As used herein, the terms listed in the following table have the corresponding meanings as indicated:

| TERM | MEANING |
|---|---|
| MS(ES) | Electron spray mass spectrometry |
| $^1$H NMR | Proton nuclear magnetic resonance spectrometry |
| J/g | joules per gram |
| TLC | thin layer chromatography |
| HPLC | high performance liquid chromatography |
| $R_f$ | retention factor |
| $R_t$ | retention time |
| AcOH | Acetic acid |
| RT | room temperature |
| DCM | dichloromethane |
| DMF | N,N-dimethylformamide |
| DMSO | methyl sulfoxide |
| LDA | lithium diisopropylamide |
| EtOAc | ethyl acetate |
| THF | tetrahydrofuran |
| iPrOAc | isopropyl acetate |
| DMAP | 4-dimethylaminopyridine |
| DBU | 1,8-diazabicyclo[5.4.0]undec-7-ene |
| Et$_3$N | triethylamine |
| (Boc)$_2$O | di-tert-butyl dicarbonate |
| MeOH | methanol |
| Triflate | —SO$_3$CF$_3$ functional group |
| (dppf) | 1,1'-bis(diphenylphosphino)ferrocene |
| S.M. | starting material |
| SCX | strong cation-exchange cartridge |
| Pd(PCy$_3$)$_2$Cl$_2$ | dichlorobis(tricyclohexylphosphine) palladium (II) |
| Pd$_2$(dba)$_3$ | tris(dibenzylideneacetone)-dipalladium(0) |
| EDCI | 1-ethyl-3-[3-(dimethylamino)propyl]-carbodiimide HCl |

Preparation 1

Propane-2-sulfonic acid{2-[4-(4,4,5,5-tetramethyl-[1,3,2]dioxaborolan-2-yl)-pheny]-thiophen-3-yl}-amide

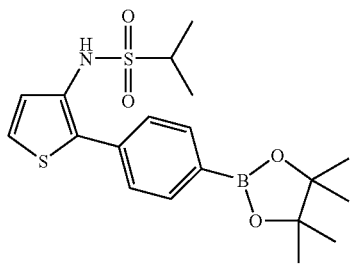

In a manner analogous to the method of Barker, J. M.; et al., *Synthetic Communications*, 25(23), 3729-3734 (1995), reflux (120° C.) methyl-3-aminothiophene-2-carboxylate (42.8 g, 0.27 mol) with 2M sodium hydroxide aqueous solution (270 mL) for 30 min. Cool the reaction mixture to 0° C. and acidify to pH 5.0 (Congo red) with concentrated hydrochloric acid. Filter the thick precipitate. Dry the solid and dissolve in acetone (300 mL) and dry the resulting solution (MgSO$_4$), filter, and evaporate at 20° C. Treat the resulting thick oil instantly with oxalic acid dihydrate (26.7 g) in 2-propanol (100 mL) at 38° C. for 45 min. Allow the mixture to reach room temperature and dilute with diethyl ether (40 mL). Filter the solid and wash with diethyl ether. The resulting white solid (33.1 g) becomes pale lilac on exposure to light and air. Dissolve the resulting salt (33.1 g) in water (400 mL) and basify with concentrated ammonium hydroxide. Extract the mixture with methylene chloride (3×200 mL) and combine the extract and dry (MgSO$_4$), filter, and evaporate to give a brown oil (15 g, 56%). Dissolve this material (15 g, 0.15 mol) in methylene chloride (300 mL) and add Et$_3$N (42.2 mL, 0.3 mol) at 0° C. Add a solution of (Boc)$_2$O (39.3 g, 0.18 mol) in methylene chloride (100 mL) dropwise at 0° C. and stir the mixture overnight at room temperature. Monitor TLC (Hexane/EtOAc 9:1) for complete disappearance of starting material. Quench the reaction by addition of water (200 mL). Extract the mixture with methylene chloride (2×200 mL) and combine the extracts, dry (MgSO$_4$), filter, and evaporate. Purify the crude by flash chromatography (Silica gel-Hexane/EtOAc 9:1) to obtain 20.1 g (67%) of (tert-butoxy)-N-(3-thiophenyl)carboxamide as a white solid.

In a manner analogous to Campaigne, E. and Monroe, P. A. *J.A.C.S.*, 76, 2447-2450 (1954), to a boiling solution of (tert-butoxy)-N-(3-thiophenyl)carboxamide (21.0 g, 0.1 mol) in methylene chloride (400 mL) add N-iodosuccinimide (23.7 g, 0.1 mol) in small portions. Set the heating bath to 65° C. for 20 min. Take the reaction to room temperature, evaporate the solvent and purify the crude by flash chromatography (Silica gel-Hexane/EtOAc 9:1) to obtain 30.0 g (88%) of (tert-Butoxy)-N-(2-iodo(3-thiophenyl))carboxamide as a white solid.

Heat (tert-Butoxy)-N-(2-iodo(3-thiophenyl))carboxamide (16.88 g, 0.52 mol), 4-bromophenylboronic acid (15.65 g, 0.78 mol), Na$_2$CO$_3$ (1.01 g, 1.04 mol) and Pd(PPh$_3$)$_4$ (5.79 g, 0.052 mol) in 375 ml of an anhydrous and deoxygenated 2:1 DME/EtOH mixture to 80° C. under nitrogen atmosphere for 24 h. Evaporate the organic solvents prior to the addition of water (200 mL). Extract the mixture with methylene chloride (3×150 mL) and combine the organic phases, dry (anh MgSO$_4$), filter, and concentrate to furnish a crude mixture as a yellowish solid. Purification by flash chromatography (Silica gel-Hexane/EtOAc 49:1) yields 10.8 g (60%) of (tert-butoxy)-N-[2-(4-bromophenyl)(3-thiophenyl)]carboxamide as a pale yellow solid.

Treat dropwise a solution of (tert-butoxy)-N-[2-(4-bromophenyl)(3-thiophenyl)]carboxamide (10.8 g, 0.3 mol) in EtOAc (75 mL) at 0° C. with 244 mL (8 mL/mmol) of freshly prepared 1N HCl in EtOAc and stir the mixture at room temperature overnight. Dissolve the white precipitate with H$_2$O (100 mL) and neutralize with a NaHCO$_3$ saturated solution. Extract the mixture with EtOAc (3×100 mL) and combine organic, dry and concentrate to give a slightly colored solid. Purification of the crude material by flash chromatography (Silica gel-Hexane/AcOEt 49:1 then 9:1) furnishes 5.7 g (74%) of 2-(4-bromo-phenyl)-thiophen-3-yl amine as a pale yellow solid.

Add slowly to a solution of 2-(4-bromo-phenyl)-thiophen-3-yl amine(0.6 g, 2.36 mmol) in dry dichloromethane (10 mL) at 0° C., DBU 1.41 mL (9.45 mmol) and isopropylsulfonyl chloride (0.53 mL, 4.72 mmol) (Temp. always <0° C.). Remove the ice bath and stir the mixture at RT overnight. Add satd. aq. NH$_4$Cl (10 mL) and extract the solution with EtOAc (2×10 mL). Dry the combined organic layers and concentrate under vacuum. Purify the crude residue by flash chromatography (Silica gel-Hexane /EtOAc 4:1) to give 0.8 g (94%) of propane-2-sulfonic acid [2-(4-bromo-phenyl)-thiophen-3-yl]-amide.

Deoxygenate by purging with nitrogen a mixture of propane-2-sulfonic acid [2-(4-bromo-phenyl)-thiophen-3-yl]-amide (1.34 g, 3.72 mmol), bis(pinacolato)diboron (1.04 g, 4.09 mmol), KOAc (1.21 g, 12.3 mmol) and Pd(dppf)Cl$_2$ (0.3 g, 0.37 mmol) in dry DMF (20 mL) and heat the mixture to 80° C. overnight. Add water (20 mL) and extract the reaction with diethyl ether (3×20 mL). Wash the combined organics with water and dry and concentrate to give a crude dark solid. Purification by flash chromatography (Silica gel-Hexane/AcOEt 7:1) gives 0.65 g (43%) of the title compound as a pale yellow solid.

Preparation 2

Propane-2-sulfonic acid (4'-(boronic acid)-biphenyl-2-yl)-amide

Add 4-bromophenyl boronic acid (5.0 g, 24.82 mmol), tetrakis(triphenylphosphine) palladium (0) (0.717 g, 0.620 mmol) and 2 M $Na_2CO_3$ (10 mL) to a solution of 2-iodoaniline (4.5 g, 20.69 mmol) in toluene (2 mL):ethanol (20 mL), deoxygenate and heat at 80° C. under nitrogen. After 4 h, add water and extract with EtOAc. Combine the organic layers, dry over sodium sulfate, filter and concentrate under reduced pressure to give a residue. Purify the residue by flash chromatography (Silica gel-EtOAc/hexane 1:12), to provide 4'-bromo-biphenyl-2-ylamine (3.53 g, 69%). MS (m/e): 248 (M+1); 249 (M+2).

Add dropwise DBU drop wise (8.76 mL, 56.92 mmol) to a solution of 4'-bromo-biphenyl-2-ylamine (3.53 g, 14.23 mmol) in dichloromethane (50 ml) at 0° C., followed by drop wise addition of isopropylsulfonyl chloride (3.29 mL, 28.46 mmol) and stir the. reaction at room temperature for 24 h. Remove solvent under reduce pressure and purify the residue by silica and eluting with EtOAc:hexane 1:4 to EtOAc to provide the title compound (4.93 g, 98%). MS (m/e): 355 (M+1); 353 (M−1).

Heat at 80° C. a mixture of propane-2-sulfonic acid (4'-bromo-biphenyl-2-yl)-amide (4.0 g, 11.22 mmol), bis(pinacolato)diboron (3.22 g, 12.34 mmol), [1,1'-bis(diphenylphosphino)ferrocene]-dichloropalladium(II) complex with dichloromethane (1:1) (0.276 g, 0.337 mmol) and potassium acetate (3.32 g, 33.87 mmol) in dry dimethylsulfoxide (25 mL). After 16 h add water and extract with EtOAc. Combine organic layers, dry over sodium sulfate and evaporate under reduce pressure. Dissolve the residue in dichloromethane and wash with a solution of 0.1N HCl. Combine the organic layers, dry over sodium sulfate, filter and concentrate under reduced pressure. Purify the residue by flash chromatography (Silica gel-EtOAc/hexane 1:3) to provide propane-2-sulfonic acid [4'-(4,4,5,5-tetramethyl-[1,3,2]dioxaborolan-2-yl)-biphenyl-2-yl]-amide (4.07 g, 90%). MS (m/e): 424 (M+23); 400 (M−1).

Add sodium periodate (1.12 g, 5.25 mmol) followed by a solution of 1 N ammonium acetate (8 mL) to a suspension of propane-2-sulfonic acid [4'-(4,4,5,5-tetramethyl-[1,3,2]dioxaborolan-2-yl)-biphenyl-2-yl)-amide (0.7 g, 1.75 mmol) in acetone (16 mL)/water (0.8 mL). Stir the mixture at room temperature under nitrogen for 20 h. Filter the precipitate and evaporate organic layer. Extract aqueous layer with dichloromethane. Combine organic layers, dry over sodium sulfate and evaporate the solvent under reduced pressure. Add hexanes and tert-butylmethyl ether to the residue until a solid is formed and filter the solid to provide the title compound (0.37 g, 67%). MS (m/e): 337 (M+18); 318 (M−1).

Preparation 3

Propane-2-sulfonic acid {4-[4-(4,4,5,5-tetramethyl-[1,3,2]dioxaborolan-2-yl)-phenyl]-pyridin-3-yl}-amide Take up 4-hydroxy-3-nitro-pyridine (6.18 g, 44.2 mmol) in phosphorus oxychloride (16 ml) and heat to 45° C. Once at 45° C., add phosphorus pentachloride (8.04 g, 38.6 mmol) in a single portion. Stir the resulting yellow slurry vigorously and heat under reflux (oil bath to 125° C.) under an inert atmosphere. After 3 h at 125° C., the yellow slurry becomes a clear yellow solution. Cool the mixture to room temperature, concentrate to an oil, cool to 0° C. in an ice bath and treat with 10 ml of water and 20 ml of dichloromethane while stirring vigorously. Basify the aqueous layer with saturated sodium bicarbonate solution and extract with dichloromethane (×3). Dry the combined organic layers over anhydrous sodium sulfate, filtered and concentrate to give 6.98 g of 4-Chloro-3-nitro-pyridine, which crystallizes on standing (99% yield).

4-Chloro-3-nitro-pyridine (6.9 g, 43.5 mmol), 4-bromophenyl boronic acid (8.05 g, 40.1 mmol), potassium carbonate (11.10 g, 80.3 mmol) and tetrakis triphenylphosphine palladium (2.31 g, 2.0 mmol) are taken up in DME (200 ml) and heated under reflux (100° C.) overnight. The mixture is cooled down to room temperature and filtered through Celite® pad, which is washed with EtOAc. The filtrate is concentrated to give a crude brown oil. Purification by flash chromatography (Silica gel-hexane/EtOAc) yields 4-(4-Bromo-phenyl)-3-nitro-pyridine (8.52 g) as a yellow oil (76% yield).

Stir 4-(4-Bromo-phenyl)-3-nitro-pyridine (8.52 g, 30.5 mmol) in glacial acetic acid (150 ml) and add 325 mesh iron powder (8.40 g, 150.4 mmol). Heat the mixture to 80° C. for 40 min at which point the mixture turns gray. Filter the mixture through Celite® and wash the solid with EtOAc. Wash the organic layer with water. Basify the aqueous layer to pH 8 with NaOH solution and extract with EtOAc (×2). Wash the combined organic layers with water, saturated aq. sodium chloride, dry over anhydrous sodium sulfate, filter and concentrate to afford 7.25 g of a brown crude oil. Purification by flash chromatography (Silica gel-hexane/EtOAc) yields 4-(4-Bromo-phenyl)-pyridin-3-ylamine (4.64 g) as a white solid (61% yield).

Take up 4-(4-Bromo-phenyl)-pyridin-3-ylamine (4.6 g, 18.5 mmol) in anhydrous dichloromethane (100 ml). Add DBU (11 ml, 73.5 mmol) and stir the solution at 0° C. for 3 min under inert atmosphere. Add isopropylsulfonyl chloride dropwise over 10 min. Allow the mixture to warm up to RT and heat under reflux (40° C.) overnight. Quench the mixture by addition of saturated ammonium chloride solution. Extract the aqueous layer with dichloromethane (×2). Wash the combined organic layers with saturated aq. sodium chloride, dry over anhydrous sodium sulfate, filter and concentrate to afford 9.1 g of a brown crude residue. Purification by flash chromatography (Silica gel-hexane/EtOAc) followed by reverse purification yields the desired compound propane-2-sulfonic acid [4-(4-bromo-phenyl)-pyridin-3-yl]-amide (2.68 g) as a white solid (41% yield).

Take up propane-2-sulfonic acid [4-(4-bromo-phenyl)-pyridin-3-yl]-amide (2.07 g, 5.8 mmol), bis(pinacolato) diboron (2.01 g, 7.9 mmol), potassium acetate (2.3 g, 23.4 mmol) and [1,1'-bis(diphenylphosphino)ferrocene]-dichloropalladium (II) complex with dichloromethane (1:1) (0.277 g, 0.339 mmol) in anhydrous DMF (12 ml) and heat to 80° C. under inert atmosphere overnight. Add water (4 ml) and filter the reaction mixture through a small pad of silica. Wash the silica pad with EtOAc. Wash the organic filtrate with HCl 0.05N, water (×4), dry over anhydrous sodium sulfate, filter and concentrate to afford 3.8 g of a dark crude residue. Purification by flash chromatography (Silica gel-hexane/EtOAc) yields the title compound (1.85 g) as a beige solid (79% yield).

Preparation 4

4'-[3-(Propane-2-sulfonylamino-thiophen-2-yl]-biphenyl-4-carboxylic acid ethyl ester

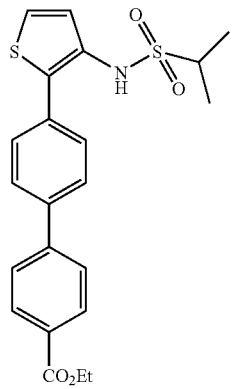

Heat in a sealed tube with stirring propane-2-sulfonic acid{2-[4-(4,4,5,5-tetramethyl-[1,3,2]dioxaborolan-2-yl)-phenyl]-thiophen-3-yl}-amide (0.5 mmol), 4-iodo-benzoic acid ethyl ester (0.75 mmol), 2M $Na_2CO_3$ water solution (0.2 mL) and $Pd(PPh_3)_4$ (0.05 mmol) in 4.0 ml of an anhydrous DME to 100° C. for 24 h. Evaporate the organic solvent, prior to the addition of water (10 mL). Extract the mixture with dichloromethane (3×20 mL) and dry the combined organic phases ($Na_2SO_4$) and concentrate to furnish a crude mixture. Purification by flash chromatography (Silica gel-hexane/EtOAc) yields the title compound.

Preparation 5

5-(4-Bromo-benzyl)-2H-tetrazole

Stir a mixture of $SiCl_4$ (1.7 g, 10 mmol, 2 eq.) and $NaN_3$ (1.95 g, 30 mmol, 6 eq.) in 50 mL of acetonitrile for 2 hours. Add 1.07 g of 2-(4-bromophenyl) acetamide (5 mmol, 1 eq.) and heat to 85° C. for 5 hour. Cool to room temperature and filter off the solid wash the solid with EtOAc. Wash the ester layer with water, saturated aq. sodium chloride, dry over $MgSO_4$ and evaporate the solvent to afford 900 mg title compound (80%). MS (m/e): 237.0.

Preparation 6

3-(4-Bromo-phenyl)-N-methyl-propionamide

Add oxalyl chloride (1.75 mL, 2.54 g, 4 eq.) to a solution of 3-(4-bromo-phenyl)-propionic acid in methylene chloride (100 mL), which contains 0.1 mL DMF at 0° C. and allow the reaction mixture to warm to room temperature and stir 1 hour. Evaporate solvent and dissolve it in 10 mL THF. Add half of the THF solution to 20 mL of methylamine (2M) and stir another hour. Add water to the solution to dissolve solid and wash organic layer with 2N HCl, water and saturated aq. sodium chloride and dry it over $MgSO_4$. Evaporate solvent to afford the title compound 500 mg, 41%. MS 246.0.

Preparation 7

Trifluoro-methanesulfonic acid 4-[1,2,4]triazol-1-yl-phenyl ester

Add pyridine (0.74 g, 9.3 mmol, 3 eq.) to a solution of 4-[1,2,4]triazol-1-yl-phenol (500 mg, 3.1 mmol, 1 eq.) at −78° C. and stir for 15 minutes. Add slowly triflic anhydride (1.05 g, 3.7 mmol, 1.2 eq.). Allow the reaction mixture to warm to room temperature and stir 3 hours. Pour the mixture into 20 mL of 1N HCl (cold). Wash the organic layer with water (2×10 mL), saturated sodium bicarbonate and saturated aq. sodium chloride. Dry and evaporate to give 860 mg (95%) of the title compound. MS. 294.0.

Preparation 8

4-Methylsulfanyl-2-trifluoromethanesulfonyloxy-benzoic acid methyl ester

Combine 2-Hydroxy-4-methylsulfanyl-benzoic acid methyl ester (5.072 g, 25.58 mmol), pyridine, and $CH_2Cl_2$ at 0° C. and stir. Add triflic anhydride (5.1 ml, 30.31 mmol) drop wise over several min. After 4 hours dilute the mixture with $CH_2Cl_2$ and wash with 1N HCl, $H_2O$, and dry over $Na_2SO_4$, filter and concentrate under reduced pressure to yield 4-Methylsulfanyl-2-trifluoromethanesulfonyloxy-benzoic acid methyl ester (7.775 g, 92%). MS (m/e): 330.8(M+1).

Preparation 9

Propane-2-sulfonic acid (4'-bromo-biphenyl-2-yl)-amide

Combine 4-bromophenylboronic acid (6.064 g, 30.195 mmol), 2-iodo-phenylamine (5.532 g, 25.257 mmol), toluene, 2N $Na_2CO_3$ (13 ml, 26 mmol), and tetrakis(triphenylphosphine)palladium(0) (0.849 g) and heat to 80° C. After 4 hours cool to room temperature and stir for 16 hours. Dilute the reaction with EtOAc and back extract water layer with EtOAc. Combine the organic layers and wash with $H_2O$, and dry over $Na_2SO4$, filter, and concentrate under reduced pressure. Purify the residue by flash chromatography (silica gel), eluting with first hexane and increasing up to 10% EtOAc/Hexane to afford 4'-bromo-biphenyl-2-ylamine (4.008 g, 64%). LCMS 247.

Add 4'-bromo-biphenyl-2-ylamine (1.038 g, 4.183 mmol) to $CH_2Cl_2$ and cool to 0° C. Add first DBU (2.6 ml, 17.038 mmol), then isopropylsulfonyl chloride (0.95 ml, 8.206 mmol) drop wise to flask and warm flask to room temperature. After 18 hours monitor reaction. If SM is still present, add DBU (1 ml), then isopropylsulfonyl chloride (0.4 ml) and then stir 2 additional hours. Purify resultant product using flash chromatography (Silica gel-25% EtOAc/Hexane) to provide propane-2-sulfonic acid (4'-bromo-biphenyl-2-yl)-amide (1.116 g, 75%). MS(m/e): 351.9(M−1).

Preparation 10

5-(4-Bromo-phenyl)-pyrazole-1-carboxylic acid tert-butyl ester

Stir a mixture of 5-(4-bromo-phenyl)-pyrazole (577 mg, 2.6 mmol, 1 eq.), di-tert-butyl-dicarbonate (737 mg. 3.38 mmol), and dimethylaminopyridine (32 mg, 0.25 mmol) in 16 mL acetonitrile overnight. Add 200 mL diethyl ether and 50 mL water. Wash the organic layer with water, saturated aq. sodium chloride and evaporate solvent to afford the title compound 800 mg, 95%.

Preparation 11

(4-Bromo-phenoxy)-acetonitrile

Mix 4-bromophenol (1.4 mmol) in acetonitrile (5 ml) and water (2 ml), add $K_2CO_3$ (3 mmol) and bromoacetonitrile (1.5 mmol) at room temperature under inert atmosphere. Heat the mixture to 80° C. for 16 h. Analyze by LC/MS for final product. Evaporate the solvent and add water. Extract product with DCM (3×) and combine and evaporate organic phases to afford the title compound.

Preparation 12

2-Bromo-5-(cyanomethyl-amino)-benzonitrile

Mix 5-amino-2-bromobenzonitrile (0.76 mmol) in anhydrous THF (3 ml), N,N-diisopropylethylamine (0.92 mmol), and bromoacetonitrile (1.0 mmol) at room temperature under inert atmosphere. Heat the mixture to 100° C. for 16 h in a sealed tube. Cool in ice bath, filter the precipitate and evaporate the filtrate to dryness to afford a crude residue. Purify by flash chromatography (Silica gel-$CHCl_3$/Ethanol/$NH_4OH$ 9:1:0.1) to yield the title compound.

Preparation 13

4-Bromo-3-(propane-2-sulfonylamino)-benzoic acid methyl ester

Add $Na_2SO_4$ (8.5 mmol) to a solution of 4-Bromo-3-nitro-benzoic acid methyl ester (1.2 mmol) in EtOH (40 mL). Heat the reaction at 70° C. for 30 min and then at room temperature overnight. Add a saturated solution of $NaHCO_3$ (pH=11-12) and extract with EtOAc (2×50 mL). Dry over $NaSO_4$, filter and evaporate to dryness to provide 4-Bromo-3-amino-benzoic acid methyl ester.

Add DBU drop wise (0.5 mmol) to a suspension of the previously prepared amine (0.1 mmol) in dichloromethane (15 ml) at 0° C., followed by drop wise addition of isopropylsulfonyl chloride (0.2 mmol) and stir the reaction at room temperature for 24 h. Remove solvent under reduce pressure. Purify by flash chromatograph (Silica gel-hexane/EtOAc). Concentrate the desired fractions to provide the title compound.

Preparation 14

4-Bromo-3-(methanesulfonylamino)-benzoic acid methyl ester

Add $Na_2SO_4$ (0.12 mmol) to a suspension of 4-Bromo-3-amino-benzoic acid methyl ester (0.1 mmol) and $Et_3N$ (0.1 mmol) in dichloromethane at 0° C. Stir 4 h at RT. Add a saturated solution of NaCl (15 mL), and extract with dichloromethane (2×50 mL). Dry over $NaSO_4$, filter and evaporate to dryness. Purify the residue utilizing flash chromatography (Silica gel-hexane/EtOAc) to provide the title compound.

Preparation 15

4'-Iodo-5-trifluoromethyl-biphenyl-2-carboxylic acid methyl ester

Heat a solution of 5-Trifluoromethyl-biphenyl-2-carboxylic acid methyl ester (1 mmol), acetonitrile and diidomethane (3.5 mmol) to 35° C. with stirring under nitrogen. Once 35° C. is reached, add i-Amylnitrite (2.5 mmol) slowly so as to avoid a large exotherm. Heat reaction to 65-70° C. for 2 hours. Remove the heat and concentrate the reaction in vacuo. Purify via radial chromatography eluting with EtOAc/dichloromethane/hexanes to yield the final product (52%). MS (m/e): 408.0 (M+1)

Preparation 16

3-Chloro-4-trifluoromethanesulfonyloxy-benzoic acid methyl ester

Add dropwise triflic anhydride (6.7 ml, 39.8 mmol) to a solution of methyl 3-chloro-4-hydroxybenzoate (5.42 g, 29.0 mmol), DMAP (490 mg, 4.0 mmol) and triethylamine (5.6 ml, 40.1 mmol) in anhydrous dichloromethane (200 ml). Stir the mixture at room temperature overnight under nitrogen atmosphere. Quench the mixture by addition of a saturated aq. solution of ammonium chloride. Separate the organic layer and extract the aqueous layer with dichloromethane (×3). Wash the combined organic layers with saturated aq. sodium chloride, dry over anhydrous sodium sulfate, filter and concentrate to yield a crude brown oil. Take up this crude oil in hexane and wash the organic layer with water (×3), dry over anhydrous sodium sulfate, filter and concentrate to. yield the title compound.

Preparation 17

4-Ethoxy-3-iodo-benzoic acid ethyl ester

To a solution of phenol in AcOH (200 mL) at 65° C., add a solution of ICl in AcOH (500 mL) dropwise. When the addition is completed, stir the mixture at 65° C. for 6 hours. After cooling, pour the mixture into ice/water, filter and wash with water. Dissolve the solid obtained in $CH_2Cl_2$, dry over $MgSO_4$, filter and concentrate in vacuo. Purify the crude product by flash chromatography (Silica gel-$CH_2Cl_2$), to obtain 131.3 g of 4-Hydroxy-3-iodo-benzoic acid ethyl ester (74% yield).

To the resultant ester (3.10 g, 10.61 mmol) and potassium carbonate (2.87 g, 20.75 mmol) in 40 ml acetonitrile, add iodoethane (1.3 ml, 16.25 mmol) at RT while stirring vigorously. Heat the resulting white suspension under reflux for 1.5 h. Evaporate acetonitrile and replace with EtOAc. Wash the organic layer first with water, then with saturated aq. sodium chloride. Dry over anhydrous sodium sulfate, filter and concentrate to give the title compound as a yellow oil.

Preparation 18

5-Bromo-1,3-difluoro-2-methoxy-benzene

Add iodomethane (2.0 ml, 32.1 mmol) dropwise to a suspension of 4-bromo-2,6-difluorophenol (5.90 g, 28.2 mmol) and potassium carbonate (4.40 g, 31.8 mmol) in acetone (50 ml) at room temperature while stirring vigorously. Heat the mixture under reflux overnight. Evaporate acetone and add dichloromethane. Filter through silica eluting the product with dichloromethane/EtOAc. Concentrate to yield the title compound.

Preparation 19

6-Bromo-2,4-difluoro-3-methoxy-benzaldehyde

Add n-butyl lithium 1.6N (22 ml, 35.2 mmol) to diisopropylamine (4.8 ml, 34.2 mmol) in anhydrous THF (7 ml) at 0° C. Stir the resulting yellow solution for 30 min at 0° C. Add this LDA solution dropwise via canula to a solution of 5-bromo-1,3-difluoro-2-methoxybenzene (5.83 g, 26.17 mmol) in anhydrous THF (40 ml) at −78° C. over 40 min. Stir the resulting bright yellow solution for 50 min at −78° C. Add anhydrous DMF (2.7 ml, 34.8 mmol) and stir the mixture for 1.5 h at −78° C. Quench the mixture with dilute sulfuric acid and extract the product with EtOAc (×3). Wash the combined organic layers with water (×3), saturated aq. sodium chloride and dry over anhydrous sodium sulfate. Filter and concentrate to yield the crude product. Purification by flash chromatography (Silica gel-hexane/EtOAc) yields the title compound.

Preparation 20

6-Bromo-2,4-difluoro-3-methoxy-benzonitrile

Add hydroxylamine hydrochloride (608 mg, 8.8 mmol) to a solution of 6-Bromo-2,4-difluoro-3-methoxy-benzaldehyde (2.0 g, 7.96 mmol) in anhydrous DMF (4 ml). Heat the mixture to 150° C. for 2 h. Add water to the cooled mixture and extract the product with EtOAc (×2). Wash the combined organic layers with water (×3), saturated aq. sodium chloride and dry over anhydrous sodium sulfate. Filter and concentrate. Dissolve the concentrate in anhydrous THF and add 3 equivalent of the Burgess reagent ((methoxycarbonylsulfamoyl)triethylammonium hydroxide, inner salt). Heat the mixture under reflux under nitrogen atmosphere overnight. Concentrate to yield a crude residue. Purification by flash chromatography (Silica gel-hexane/EtOAc) yields the title compound.

Preparation 21

3-Bromo-4-cyano-benzoic acid methyl ester

Dissolve 4-bromo-3-nitro-benzoic acid methyl ester (4.25 g, 16.3 mmol) in ethanol (100 ml) and water (30 ml). Add sodium dithionite (15 g, 75 mmol) in a single portion and heat the mixture under reflux for 4 h. Evaporate ethanol and add water. Basify the aqueous layer with 10% sodium carbonate solution. Extract the product with EtOAc (×2). Dry the combined organic layers over anhydrous sodium sulfate, filter and concentrate to yield 3-amino-4-bromo-benzoic acid methyl ester (51%).

Add zinc cyanide (1.5 g, 12.77 mmol), palladium tetrakis (675 mg, 0.584 mmol), to 3-amino-4-bromo-benzoic acid methyl ester (1.328 g, 5.77 mmol) in anhydrous DMF (3 ml). Purge with nitrogen for few minutes and keep under nitrogen atmosphere while heating to 120° C. overnight. Cool the mixture to room temperature and add water. Extract the product with EtOAc (×2). Wash the combined organic layers with 2N ammonium hydroxide solution (×2), water (×2), saturated aq. sodium chloride and dry over anhydrous sodium sulfate, filter and concentrate to yield the crude product. Purification by flash chromatography (Silica gel-hexane/EtOAc) yields 3-amino-4-cyano-benzoic acid methyl ester (94%).

Add 3-amino-4-cyano-benzoic acid methyl ester (1.1 g, 6.24 mmol) to a stirred solution of sodium nitrite (511 mg, 7.4 mmol) in concentrated sulfuric acid (5 ml) and glacial acetic acid (5 ml) at 40° C. After 30 min at 40° C., pour the resulting orange solution into a cold solution of copper bromide (1.42 g, 9.89 mmol) in 48% hydrobromic acid (5 ml). When the evolution of nitrogen is finished, heat the mixture to 90° C. for 30 min. Cool down to room temperature and pour the mixture onto crushed ice. Filter out the resulting dark solid, wash with water. Take this solid up in chloroform and filter the inorganic solid. Concentrate the filtrate to yield a crude yellow residue. Purification by flash chromatography (Silica gel-hexane/EtOAc) yields the title compound (56%).

Preparation 22

2.2-Dimethyl-propionic acid 4-bromo-2,6-difluoro-phenyl ester

Add triethylamine (10.0 ml, 71.7 mmol) to 4-bromo-2,6-difluorophenol (9.92 g, 47.4 mmol) in anhydrous dichloromethane (100 ml) at 0° C. while stirring under inert atmosphere. Add pivaloyl chloride (8 ml, 64.9 mmol) dropwise over 10 min. Allow the solution to warm up to room temperature overnight. Add water and extract the aqueous layer with dichloromethane (×2). Wash the combined organic layers with water (×2), saturated aq. sodium chloride, dry over anhydrous sodium sulfate, filter and concentrate to afford 15.5 g of a clear crude oil. Purification by flash chromatography (Silica gel-hexane /diethyl ether) yields the title compound (13.1 g) as a clear oil (94% yield).

Preparation 23

2,2-Dimethyl-propionic acid 4-bromo-2,6-difluoro-3-formyl-phenyl ester

Add n-butyl lithium 1.6N (23 ml, 36.8 mmol) to diisopropylamine (5.0 ml, 35.6 mmol) in anhydrous THF (7 ml) at 0° C. Stir the resulting yellow solution for 30 min at 0° C. Add this LDA solution dropwise via canula to a solution of 2,2-Dimethyl-propionic acid 4-bromo-2,6-difluoro-phenyl ester (8.01 g, 27.33 mmol) in anhydrous THF (40 ml) at −78° C. over 40 min. Stir the resulting bright yellow solution for 1 h at −78° C. Add anhydrous DMF (2.8 ml, 35.0 mmol) and stir the mixture for 1.5 h at −78° C. Quench the mixture with dilute sulfuric acid and extract the product with EtOAc (×3). Wash the combined organic layers with water (×3), saturated aq. sodium chloride and dry over anhydrous sodium sulfate. Filter and concentrate to yield the crude product. Purification by flash chromatography (Silica gel-hexane/EtOAc) yields 8.35 g of the title compound (95% yield).

Preparation 24

2,2-Dimethyl-propionic acid 4-bromo-3-cyano-2,6-difluoro-phenyl ester

Add hydroxylamine hydrochloride (2.33 g, 33.6 mmol) and sodium iodide (2.09 g, 13.96 mmol) to a solution of 2,2-Dimethyl-propionic acid 4-bromo-2,6-difluoro-3-formyl-phenyl ester (8.34 g, 25.97 mmol) in acetonitrile (100 ml). Heat the mixture under reflux (100° C.) for 3 h. TLC (Hexane:Ethyl Acetate 4:1) shows incomplete conversion. Cool down the mixture to 60° C. and add more hydroxylamine hydrochloride (2.24 g, 33.0 mmol). Heat the mixture to 100° C. for 1.5 h.

Quench the mixture with 5% aqueous Na2S2O3 and stir for 5 min until the red-brown color has disappeared. Extract the product with ethyl acetate (×2). Wash the combined organic layers with water (×3), saturated aq. sodium chloride and dry over anhydrous sodium sulfate. Filter and concentrate. Dissolve the concentrate in anhydrous THF and add 1.7 equivalent of the Burgess reagent ((methoxycarbonylsulfamoyl)triethylammonium hydroxide, inner salt) (10.0 g, 41.96 mmol). Heat the mixture under reflux under nitrogen atmosphere for 4 h. Concentrate to yield a crude residue. Purification by flash chromatography (Silica gel-hexane/EtOAc) yields 5.87 g of the title compound as a pale yellow solid (75% yield).

Preparation 25

Propane-2-sulfonic acid [2-(4-bromo-phenyl)-2H-pyrazol-3-yl]-amide

Add DBU (5.14 mL, 33.69 mmol) to a solution of 5-amino-1-(4-bromo-phenyl)-1H-pyrazole-4-carboxylic acid ethyl ester (2.612 g, 8.42 mmol) in dichloromethane (25 mL) at 0° C. Stir for 15 min. at 0° C. and then add isopropylsulfonyl chloride (1.94 mL, 16.84 mmol). Immerse the mixture into a pre-heated oil bath (50° C.). After stirring for 5 min., add additional isopropylsulfonyl chloride (0.97 mL, 8.42 mmol). Stir overnight at 50° C. Add 1.0M HCl (aq) until pH 5, wash with water (2×50 mL), dry over sodium sulfate, filter, and concentrate. Adsorb the compound onto silica gel, and subject to silica gel flash column chromatography (15-30% EtOAc/n-hexane) to yield 1-(4-Bromo-phenyl)5-(propane-2-sulfonylamino)-1H-pyrazole-4-carboxylic acid ethyl ester (2.55 g, 73%).

Dissolve 1-(4-Bromo-phenyl)5-(propane-2-sulfonylamino)-1H-pyrazole-4-carboxylic acid ethyl ester (2.549 g, 6.12 mmol) in ethanol (10 mL)(denatured with methanol) and then add an aqueous solution of sodium hydroxide (12.5 mL, 2.0M). Immerse the resulting mixture into a pre-heated oil bath (65° C.) and stir overnight. Upon completion, concentrate to remove ethanol/methanol, wash the resulting aqueous mixture with dichloromethane, and concentrate to remove any trace of dichloromethane. Cool the aqueous mixture to 0° C., add 1.0 HCl until pH 4 is achieved (extensive precipitation of acid may be observed), and stir for 15 min. Filter the mixture under reduced pressure. Allow the reduced pressure to cool the filtrate, and filter a second crop of product. Combine the two crops to yield 1-(4-Bromo-phenyl)-5-(propane-2-sulfonylamino)-1H-pyrazole-4-carboxylic acid (2.031 g, 85%).

Dissolve 1-(4-Bromo-phenyl)-5-(propane-2-sulfonylamino)-1H-pyrazole-4-carboxylic acid (1.952 g, 5.03 mmol) in quinoline (2.79 mL) in a sealed tube. Add copper (0.16 g, 2.51 mmol) and immerse into a pre-heated (180° C.) oil bath and stir for 15 min. Cool to room temperature and remove the solvent under reduced pressure. Dilute with dichloromethane, wash with 1.0M HCl (2×50 mL), dry over sodium sulfate, filter, and concentrate to yield a residue. Subject to silica gel flash column chromatography (15-55% EtOAc/n-hexane) to yield the title compound (1.323 g, 76%).

EXAMPLE 1

Propane-2-sulfonic acid-(2-biphenyl-4-yl-thiophen-3-yl)-amide

Heat in a sealed tube with stirring propane-2-sulfonic acid [2-(4-bromo-phenyl)-thiophen-3-yl]-amide (0.5 mmol), phenyl boronic acid (0.75 mmol), 2M $Na_2CO_3$ water solution (0.2 mL) and $Pd(PPh_3)_4$ (0.05 mmol) in 4.0 ml of an anhydrous and deoxygenated 2:1 DME/EtOH mixture to 80° C.-100° C. for 24 h. Filter mixture through a small silica pad and elute with EtOAc. Evaporate the filtrate. Purify the product by flash chromatography (Silica gel-hexane/EtOAc) to obtain the title compound. MS (ES−): 356 (M−1).

Prepare the following compounds in a manner analogous to the procedure set forth in the above example:

| EXAMPLE | COMPOUND | DATA MS (ES−): |
|---|---|---|
| 2 | Propane-2-sulfonic acid [2-(4'-amino-biphenyl-4-yl)-thiophen-3-yl]-amide | 371 (M − 1) |
| 3 | Propane-2-sulfonic acid [2-(2'-cyano-biphenyl-4-yl)-thiophen-3-yl]-amide | 381 (M − 1) |
| 4 | N-{4'-[3-(Propane-2-sulfonylamino)-thiophen-2-yl]-biphenyl-3-yl}-acetamide | 413 (M − 1) |
| 5 | Propane-2-sulfonic acid [2-(3'-methanesulfonyl-amino-biphenyl-4-yl)-thiophen-3-yl]-amide | 449 (M − 1) |
| 6 | N-[2-(Propane-2-sulfonylamino)-[1,1';4',1'']terphenyl-3''-yl]-acetamide | 407 (M − 1) |
| 7 | Propane-2-sulfonic acid [3''-(propane-2-sulfonylamino)-[1,1';4',1''] terphenyl-2-yl]-amide | 443 (M − 1) |
| 8 | N-{2-Cyano-4'-[3-(propane-2-sulfonylamino)-thiophen-2-yl]-biphenyl-4-yl}-acetamide | 438 (M − 1) |
| 9 | Propane-2-sulfonic acid [2-(2'-cyano-4'-hydroxy-biphenyl-4-yl)-thiophen-3-yl]-amide | 397 (M − 1) |
| 10 | Propane-2-sulfonic acid {2-[2'-cyano-4'-(cyanomethyl-amino)-biphenyl-4-yl]-thiophen-3-yl}-amide | 435 (M − 1) |
| 11 | Propane-2-sulfonic acid [2-(3',5'-difluoro-4'-hydroxy-biphenyl-4-yl)-thiophen-3-yl]-amide | 408 (M − 1) |
| 12 | N-{2-Cyano-4'-[3-(propane-2-sulfonylamino)-pyridin-4-yl]-biphenyl-4-yl}-acetamide | 433 (M − 1) |
| 13 | Propane-2-sulfonic acid [4-(2'-cyano-biphenyl-4-yl)-pyridin-3-yl]-amide | 376 (M − 1) |
| 14 | Propane-2-sulfonic acid [2-(2'-cyano-3',5'-difluoro-4'-hydroxy-biphenyl-4-yl)-thiophen-3-yl]-amide | 433 (M − 1) |

Prepare the following compounds in a manner analogous with the procedure set forth in Example 1. Extract the resultant compound in ethyl acetate, wash the organic layer with water three times, dry over $MgSO_4$, filter, and concentrate to obtain the title compound.

| EXAMPLE | COMPOUND | DATA MS (ES−): |
|---|---|---|
| 15 | Propane-2-sulfonic acid [2-(4'-acetyl-2'-cyano-biphenyl-4-yl)-thiophen-3-yl]-amide | 423 (M − 1) |
| 16 | 2-{4'-[3-(Propane-2-sulfonylamino)-thiophen-2-yl]-biphenyl-4-yl}-acetamide | 436 (M − 1) |

Prepare the following compounds in a manner analogous with the procedure set forth in Preparation 4:

| EXAMPLE | COMPOUND | DATA MS (ES−): |
|---|---|---|
| 17 | 4'-[3-(Propane-2-sulfonylamino)-thiophen-2-yl]-biphenyl-3-sulfonic acid amide (PdCl$_2$dppf) | MS (ES+, m/e): 437 (M + 1) |
| 18 | 4'-[3-(Propane-2-sulfonylamino)-thiophen-2-yl]-biphenyl-4-sulfonic acid amide (PdCl$_2$dppf) | MS (ES+, m/e): 437 (M + 1) |
| 19 | Propane-2-sulfonic acid [2-(4'-fluoro-biphenyl-4-yl)-thiophen-3-yl]-amide | 374 (M − 1) |
| 20 | Propane-2-sulfonic acid [2-(4'-acetyl-biphenyl-4-yl)-thiophen-3-yl]-amide | 398 (M − 1) |
| 21 | Propane-2-sulfonic acid [2-(2',4'-difluoro-biphenyl-4-yl)-thiophen-3-yl]-amide | 392 (M − 1) |

-continued

| EXAMPLE | COMPOUND | DATA MS (ES−): |
|---|---|---|
| 22 | N-{2-Fluoro-4'-[3-(propane-2-sulfonylamino)-thiophen-2-yl]-biphenyl-4-yl}-acetamide | 431 (M − 1) |
| 23 | Propane-2-sulfonic acid [2-(2'-cyano-4'-fluoro-biphenyl-4-yl)-thiophen-3-yl]-amide | 399 (M − 1) |
| 24 | Propane-2-sulfonic acid [2-(2',4'-dicyano-biphenyl-4-yl)-thiophen-3-yl]-amide | 406 (M − 1) |
| 25 | Propane-2-sulfonic acid [2-(2'-cyano-4'-nitro-biphenyl-4-yl)-thiophen-3-yl]-amide | 426 (M − 1) |
| 26 | Propane-2-sulfonic acid [2-(4'-amino-2'-cyano-biphenyl-4-yl)-thiophen-3-yl]-amide | 398 (M − 1) |
| 27 | Propane-2-sulfonic acid [2-(3'-cyanomethyl-biphenyl-4-yl)-thiophen-3-yl]-amide | 395 (M − 1) |

EXAMPLE 28

Propane-2-sulfonic acid {2-[4'-(2-hydroxy-ethyl)-biphenyl-4-yl]-thiophen-3-yl}amide Mix propane-2-sulfonic acid{2-[4-(4,4,5,5-tetramethyl-[1,3,2]dioxaborolan-2-yl)-phenyl]-thiophen-3-yl}-amide (0.10 g), 0.1 equiv of tetrakis triphenylphosphine palladium (0), 2 equiv of 2M sodium carbonate aqueous solution in DME (2 mL) and EtOH(1 mL) and warm to 90-95° C. After warming two min, add 2-(4-bromo-phenyl)-ethanol (1.3 equiv) and stir at that temperature for 1.5 h. Evaporate solvents over Celite® and purify by silica gel Strata® cartridges eluting with hexanes-EtOAc gradient to give 0.041 g of the title compound. MS (ES+) (m/z): 402 (M+1).

EXAMPLE 29

6-(Propane-2-sulfonylamino)-4'-[3-(propane-2-sulfonylamino)-thiophen-2-yl]-biphenyl-2-carboxylic acid Heat the mixture of propane-2-sulfonic acid {2-[4-{4,4,5,5-tetramethyl-[1,3,2]dioxaborolan-2-yl)-phenyl]-thiophen-3-yl}-amide(662 mg, 1.65 mmol), 2-bromo-3-nitro-benzoic acid methyl ester (390 mg, 1.5 mmol), Na$_2$CO$_3$(2M, 2.2 mL, 4.5 mmol) and Pd(PPh$_3$)$_4$ (260 mg, 0.26 mmol) and 15 ml of 1,4 dioxane under N$_2$ to 80° C. overnight. After cooling to room temperature, dilute with diethyl ether (200 mL). Wash with water, saturated aq. sodium chloride, and dry over MgSO$_4$. Remove solvent and purify by flash chromatography (Silica gel-hexane/EtOAc) to provide 6-nitro-4'-[3-(propane-2-sulfonylamino)-thiophen-2-yl]-biphenyl-2-carboxylic acid methyl ester (250 mg). MS (m/e): 478.7(M+1).

Add SnCl$_2$ 2 H$_2$O (470 mg, 2.8 mmol) to a solution of 6-nitro-4'-[3-(propane-2-sulfonylamino)-thiophen-2-yl]-biphenyl-2-carboxylic acid methyl ester (250 mg, 0.54 mmol) in EtOH (5 mL). Heat the reaction at 80° C. for 3 hours. Add 100 mL EtOAc and wash it with a saturated solution of NaHCO$_3$, water and saturated aq. sodium chloride (50 mL). Dry over NaSO$_4$, filter and evaporate to dryness to provide 6-amino-4'-[3-(propane-2-sulfonylamino)-thiophen-2-yl]-biphenyl-2-carboxylic acid methyl ester (208 mg). MS (m/e): 429.1(M−1).

Add 1,8-diazabicyclo [5.4.0] undec-7-ene (DBU) drop wise (0.51 mL, 3.6 mmol) to a suspension of 6-amino-4'-[3-(propane-2-sulfonylamino)-thiophen-2-yl]-biphenyl-2-carboxylic acid methyl ester (208 mg 0.48 mmol) in dichloromethane (9 ml) at 0° C., followed by drop wise addition of isopropylsulfonyl chloride (0.21 mL, 0.9 mmol) and stir the reaction at room temperature overnight. Remove solvent under reduced pressure. Purify with flash chromatography (Silica gel-hexane/EtOAc). Concentrate the desired fractions to provide 6-(propane-2-sulfonylamino)-4'-[3-(propane-2-sulfonylamino)-thiophen-2-yl]-biphenyl-2-carboxylic acid methyl ester (50 mg). MS (m/e): 535.1(M−1).

Heat the mixture of 6-(propane-2-sulfonylamino)-4'-[3-(propane-2-sulfonylamino)-thiophen-2-yl]-biphenyl-2-carboxylic acid methyl ester (46 mg, 0.08 mmol) and LiOH (30 mg, 1.25 mmol) in 3 ml of THF/Methanol/water (3/2/1, v/v/v) to 60 C for 3 h. Remove solvent and dissolve in water (35 mL). Wash with methylene chloride (2×20 mL). Neutralize the aq. solution to a pH between 2 and 3. Further purification with flash chromatography affords the title compound. MS (m/e): 521.1(M−1).

EXAMPLE 30

Propane-2-sulfonic acid {2-[4'-(2H-tetrazol-5-ylm-ethyl)-biphenyl-4-yl]-thiophen-3-yl}-amide Deoxygenate and heat a mixture of trifluoro-methane-sulfonic acid 4'-(5H-tetrazol-5-ylmethyl)-biphenyl-4-yl ester (48mg, 0.2 mmol), propane-2-sulfonic acid {2-[4-(4,4,5,5-tetramethyl-[1,3,2] dioxaborolan-2-yl)-phenyl]-thiophen-3-yl}-amide (95 mg, 0.24 mmol, 1.2 eq.), barium hydroxide octahydrate(189 mg, 0.6 mmol, 3 eq.) and Pd(dffp)(29 mg, 0.04 mmol, 0.2 eq.) in 2 ml DMF and water mixture (4/1, v/v) to 80° C. overnight. Cool the mixture to room temperature and dilute with 30 mL EtOAc. Wash with water (3×10mL) and saturated aq. sodium chloride, dry, and remove solvent. Purification by flash chromatography (Silica gel-CH$_2$Cl$_2$: MeOH(1/50, v/v)) affords the title compound 50 mg(53%). MS (m/e): 441.1(M+1).

Prepare the following compounds in a manner substantially analogous to the procedure set forth in the above example:

| EXAMPLE | COMPOUND | DATA MS (ES−): |
|---|---|---|
| 31 | {4'-[3-(Propane-2-sulfonylamino)-thiophen-2-yl]-biphenyl-4-yl}-acetic acid | 414.1 (M − 1) |
| 32 | 2-{4'-[3-(Propane-2-sulfonylamino)-thiophen-2-yl]-biphenyl-4-yl}-acetamide | 413.2 (M − 1) |
| 33 | 3-{4'-[3-(Propane-2-sulfonylamino)-thiophen-2-yl]-biphenyl-4-yl}-propionic acid | 428.1 (M − 1) |
| 34 | Propane-2-sulfonic acid [2-(4'-[1,2,4]triazol-1-yl-biphenyl-4-yl)-thiophen-3-yl]-amide | 425.0 (M + 1) |

EXAMPLE 35

{4'-[3-(Propane-2-sulfonylamino)-thiophen-2-yl]-biphenyl-4-yloxy}-acetic acid

Heat a solution of (4-Iodo-phenoxy)-acetic acid or (4-bromo-phenoxy)-acetic acid (0.25 mmol), propane-2-sulfonic acid {2-[4-(4,4,5,5-tetramethyl-[1,3,2]dioxaborolan-2-yl)-phenyl]-thiophen-3-yl}-amide (122 mg, 0.30 mmol), PdCl$_2$(dppf)(41 mg, 0.05 mmol) and barium hydroxide (158 mg, 0.50 mmol) in DMF-H$_2$O (v/v 4:1, 2.5 mL) to 80° C. under nitrogen atmosphere for 20 h. Pour into H$_2$O (50 mL) and dichloromethane (50 mL), then extract with H$_2$O (4×50 mL) and dry the combined organic phases (MgSO$_4$). Concentrate to furnish a crude mixture as a yellowish solid. Purification by flash chromatography (Silica gel-Hexane/EtOAc)

affords the title compound as a pale yellow solid (65-80% yield). MS (ES−):430.1 (M−1).

Prepare the following compound in a manner analogous to the procedure set forth in the above example:

| EXAMPLE | COMPOUND | DATA MS (ES−): |
|---|---|---|
| 36 | {4'-[3-(Propane-2-sulfonylamino)-thiophen-2-yl]-biphenyl-4-ylsulfanyl}-acetic acid | 446.1 (M − 1) |

EXAMPLE 37

2-Chloro-4'-[3-(propane-2-sulfonylamino)-thiophen-2-yl]-biphenyl-4-carboxylic acid Heat in a sealed tube with stirring propane-2-sulfonic acid{2-[4-(4,4,5,5-tetramethyl-[1,3,2]dioxaborolan-2-yl)-phenyl]-thiophen-3-yl}-amide (0.5 mmol), 3-chloro-4-trifluoromethanesulfonyloxy-benzoic acid (0.75 mmol), 2M $Na_2CO_3$ aq. solution (0.2 mL) and $Pd(PPh_3)_4$ (0.05 mmol) in 4.0 ml of a mixture of DME: Ethanol (2:1) to 80° C. for 24 h. Filter the mixture through a small silica pad and eluted with EtOAc. Evaporate the filtrate and purify resultant compound by flash chromatography (Silica gel-hexane/EtOAc).

Add NaOH 2M (1 ml) to the resultant ester (0.128 mmol) in ethanol (1 ml) and stir 24 h. Add 6N HCl until pH is approximately 1 and a white solid precipitates. Filter the solid to provide the title compound. MS (ES−): 435 (M−1).

Prepare the following compounds in a manner analogous with the procedure set forth in the above example:

| EXAMPLE | COMPOUND | DATA MS (ES−): |
|---|---|---|
| 38 | 4-Cyano-4'-[3-(propane-2-sulfonylamino)-thiophen-2-yl]-biphenyl-2-carboxylic acid | 425 (M − 1) |
| 39 | 2-Methoxy-4'-[3-(propane-2-sulfonylamino)-thiophen-2-yl]-biphenyl-4-yl}-acetic acid | 444 (M − 1) |
| 40 | 6-Cyano-4'-[3-(propane-2-sulfonylamino)-thiophen-2-yl]-biphenyl-3-carboxylic acid | 435 (M − 1) |
| 41 | 4'-[3-(Propane-2-sulfonylamino)-thiophen-2-yl]-biphenyl-3-carboxylic acid | 400 (M − 1) |
| 42 | {2-Fluoro-4'-[3-(propane-2-sulfonylamino)-thiophen-2-yl]-biphenyl-4-yl}-acetic acid | 432 (M − 1). |
| 43 | 2''-(Propane-2-sulfonylamino)-5-trifluoromethyl-[1,1';4',1'']terphenyl-2-carboxylic acid | MS (m/e): 481.2 (M + 17); 462.2 (M − 1) |
| 44 | 2''-Chloro-2-(propane-2-sulfonylamino)-[1,1';4'1'']terphenyl-4''-carboxylic acid | 428 (M − 1) |
| 45 | 2''-Cyano-2-(propane-2-sulfonylamino)-[1,1';4',1'']terphenyl-4''-carboxylic acid | 419 (M − 1) |
| 46 | 2''-Methoxy-2-(propane-2-sulfonylamino)-[1,1';4',1'']terphenyl-4''-carboxylic acid | 424 (M − 1) |
| 47 | 2''-(Propane-2-sulfonylamino)-[1,1';4',1'']terphenyl-4''-carboxylic acid | 394 (M − 1) |
| 48 | 6''-Ethoxy-2-(propane-2-sulfonylamino)-[1,1';4',1'']terphenyl-3''-carboxylic acid | 438 (M − 1) |
| 49 | 6''-Cyano-2-(propane-2-sulfonylamino)-[1,1';4',1'']terphenyl-3''-carboxylic acid | 419 (M − 1) |
| 50 | 2-(Propane-2-sulfonylamino)-[1,1';4',1'']terphenyl-3''-carboxylic acid | 394 (M − 1) |
| 51 | 2-Cyano-4'-[3-(propane-2-sulfonylamino)-pyridin-4-yl]-biphenyl-4-carboxylic acid | 420 |
| 52 | 2-Methoxy-4'-[3-(propane-2-sulfonylamino)-thiophen-2-yl]-biphenyl-4-carboxylic acid | 430 (M − 1) |

EXAMPLE 53

4'-[3-(Propane-2-sulfonylamino)-thiophen-2-yl]-biphenyl-4-carboxylic acid

Add NaOH 2M (1 ml) to a suspension of 4'-[3-(propane-2-sulfonylamino)-thiophen-2-yl]-biphenyl-4-carboxylic acid ethyl ester (0.128 mmol) in ethanol (1 ml) and stir 24 h. Add 6N HCl until pH is approximately 1 and a white solid precipitates. Filter the solid to provide the title compound: MS (ES−): 400 (M−1).

Prepare the following compound in a manner analogous with the procedure set forth in the above example:

| EXAMPLE | COMPOUND | DATA MS (ES−): |
|---|---|---|
| 54 | 2-(Propane-2-sulfonylamino)-4'-[3-(propane-2-sulfonylamino)-thiophen-2-yl]-biphenyl-4-carboxylic acid | 521 (M − 1) |

EXAMPLE 55

Propane-2-sulfonic acid [2-(5'-amino-2'-cyano-biphenyl-4-yl)-thiophen-3-yl]-amide Prepare propane-2-sulfonic acid [2-(2'-cyano-5'-nitro-biphenyl-4-yl)-thiophen-3-yl]-amide in a manner analogous to the procedure set forth in Preparation 4. Add $SnCl_2.2 H_2O$ (642 mg, 3.40 mmol) into a solution of propane-2-sulfonic acid [2-(2'-cyano-5'-nitro-biphenyl-4-yl)-thiophen-3-yl]-amide (279 mg, 0.654 mmol) in ethanol (6.54 mL). Heat the mixture at 90° C. for 3 h. Cool to room temperature. Concentrate to remove the solvent in vacuo. Dilute with dichloromethane, and add aqueous sodium bicarbonate solution to adjust pH to 8. Extract with with dichloromethane (3×100 mL) and dry the combined organic layers and concentrate to give a slightly colored solid. Purification by flash chromatography (Silica gel-Hexane/EtOAc 2:1) furnishes 212 mg, 0.534 mmol (82%) of title compound as a pale yellow solid. MS (m/e): 396.1 (M−1).

EXAMPLE 56

Propane-2-sulfonic acid [2-(2'-cyano-3',5'-difluoro-4'-hydroxy-biphenyl-4-yl)-thiophen-3-yl]-amide Heat in a sealed tube with stirring propane-2-sulfonic acid{2-[4-(4,4,5,5-tetramethyl-[1,3,2]dioxaborolan-2-yl)-phenyl]-thiophen-3-yl}-amide (0.5 mmol), 6-bromo-2,4-difluoro-3-hydroxy-benzonitrile (0.75 mmol), 2M $Na_2CO_3$ water solution (0.2 mL) and $Pd(PPh_3)_4$ (0.05 mmol) in 4.0 ml of a mixture of DME: Ethanol (2: 1) to 80° C. for 24 h. Filter the mixture through a small silica pad and eluted with EtOAc. Evaporate the filtrate and purify resultant compound by flash chromatography (Silica gel-methanol).

Stir the resultant product (271 mg, 0.604 mmol) with tetrabutylammonium iodide (313 mg, 0.847 mmol) in anhydrous dichloromethane at −78° C. under nitrogen atmosphere. Add a solution of boron trichloride 1N in dichloromethane (5.0 ml, 5 mmol) over 2 min. Stir the resulting brown mixture for 5 min at −78° C. and allow the mixture to warm up to room temperature over 1 h. Quench the reaction with crushed ice, stir for 30 min, neutralize with saturated aqueous solution of sodium bicarbonate until pH 7 and extract the product with dichloromethane (×3). Wash the combined organic layers with water (×3), saturated aq. sodium chloride and dry over anhydrous sodium sulfate. Filter and concentrate to yield a crude brown oil. Purification by flash chromatography (Silica gel-hexane/EtOAc) and reverse phase purification yield the title compound. MS (ES−): 433(M−1).

EXAMPLE 57

4-Oxo-4-{4'-[3-(propane-2-sulfonylamino)-thiophen-2-yl]-biphenyl-4-yl}-butyric acid Heat in a sealed tube with stirring propane-2-sulfonic acid{2-[4-(4,4,5,5-tetramethyl-[1,3,2]dioxaborolan-2-yl)-phenyl]-thiophen-3-yl}-amide (0.5 mmol), 4-(4-Bromo-phenyl)-4-oxo-butyric acid (0.75 mmol), 2M $Na_2CO_3$ water solution (0.2 mL) and $Pd(PPh_3)_4$ (0.05 mmol) in 4.0 ml of an anhydrous DME to 100° C. for 24 h. Evaporate and purify the filtrate by flash chromatography (Silica gel-hexane/EtOAc). Add NaOH 2M (1 ml) to a suspension of the resultant ester (0.128 mmol) in ethanol (1 ml) and stir 24 h. Add 6N HCl until pH is approximately 1 and a white solid precipitates. Filter the solid to provide the title compound. MS (ES−): 456 (M−1).

Prepare the following compounds in a manner analogous to the procedure set forth in the above example:

| EXAMPLE | COMPOUND | DATA MS (ES−): |
|---|---|---|
| 58 | Propane-2-sulfonic acid [2-(4'-chloro-2'-fluoro-biphenyl-4-yl)-thiophen-3-yl]-amide | 418 (M − 1) |
| 59 | 2-Cyano-4'-[3-(propane-2-sulfonylamino)-thiophen-2-yl]-biphenyl-4-carboxylic acid | 425 (M − 1) |
| 60 | 2-Methyl-4'-[3-(propane-2-sulfonylamino)-thiophen-2-yl]-biphenyl-4-carboxylic acid | 414 (M − 1) |
| 61 | 2-Hydroxy-4'-[3-(propane-2-sulfonylamino)-thiophen-2-yl]-biphenyl-4-carboxylic acid | 416 (M − 1) |
| 63 | 2-Isopropoxy-4'-[3-(propane-2-sulfonylamino)-thiophen-2-yl]-biphenyl-4-carboxylic acid | 458 (M − 1) |
| 64 | 2''-Ethoxy-2-(propane-2-sulfonylamino)-[1,1';4',1'']terphenyl-4''-carboxylic acid | 438 (M − 1) |
| 65 | 2''-Fluoro-2-(propane-2-sulfonylamino)-[1,1';4',1'']-terphenyl-4''-carboxylic acid | 412 (M − 1) |
| 66 | 2-(Propane-2-sulfonylamino)-[1,1';4',1'']terphenyl-4''-carboxylic acid | 394 (M − 1) |

EXAMPLE 67

{6-Cyano-4'-[3-(propane-2-sulfonylamino)-thiophen-2-yl]-biphenyl-3-yloxy}-acetic acid Heat (3-chloro-4-cyano-phenoxy)-acetic acid ethyl ester (120 mg, 0.50 mmol), propane-2-sulfonic acid {2-[4-(4,4,5,5-tetramethyl-[1,3,2]dioxaborolan-2-yl)-phenyl]-thiophen-3-yl}-amide (204 mg, 0.50 mmol), 2 M aqueous $Na_2CO_3$ solution (0.75 mL) and $Pd(PCy_3)_2Cl_2$(55.4 mg, 0.075 mmol) in 1,4-dioxane (3.0 mL) to 80° C. under nitrogen atmosphere for 20 h. Pour into 0.1 M HCl solution and adjust pH to 7, then extract with diethyl ether (3×50 mL) and dry the combined organic phases ($MgSO_4$) and concentrate to furnish a crude mixture as a yellowish solid. Purification by flash chromatography (Silica gel-Hexane /diethyl ether 1:1) yields 201 mg, 0.42 mmol (83%) of {6-Cyano-4'-[3-(propane-2-sulfonylamino)-thiophen-2-yl]-biphenyl-3-yloxy}-acetic acid ethyl ester as a pale yellow solid.

Prepare aqueous LiOH solution by dissolving 50 mg of LiOH in 1.0 mL of water. Add aqueous LiOH solution slowly to a solution of the above prepared ester (200 mg, 0.415 mmol) in THF (2.0 mL) and MeOH (1.0 mL). Stir the mixture at 60° C. for 3 h. Concentrate to remove the solvent. Dilute in $H_2O$ (50 mL). Wash with dichloromethane (2×50 mL). Add 0.1 M HCl solution to adjust pH to 3. Extract with dichloromethane (2×50 mL) and diethyl ether (2×50 mL). Dry the combined organics and concentrate under reduced pressure to yield 137 mg, 0.300 mmol (72%) of the title compoundt. MS (m/e): 455.1 (M−1).

EXAMPLE 68

Propane 2-sulfonic acid (2 ''-cyano-[1,1', 4', 1'']terphenyl-2-yl)-amide

Heat in a sealed tube with stirring propane-2-sulfonic acid (4'-bromo-biphenyl-2-yl)-amide (0.5 mmol), 2-(cyanophenyl)boronic acid (0.75 mmol), $K_3PO_4.H_2O$ (1.8 mmol) $PPh_3$ (0.12 mmol) and $Pd(OAc)_2$ (0.06 mmol) in 3.0 ml anhydrous deoxygenated 1,4 dioxane to 110° C. for 4 h. Cool reaction mixture and maintain at RT overnight. Add EtOAc and water and extract. Extract the aqueous phase with dichloromethane (3×20 mL) and dry the combined organic phases ($Na_2SO_4$) and concentrate to furnish a crude mixture. Purification by flash chromatography (Silica gel-hexane/EtOAc) yields the title compound. MS (ES−): 375(M−1). Prepare the following compound in a manner substantially analogous to the procedure set forth in the above example:

| EXAMPLE | COMPOUND | DATA MS (ES−): |
|---|---|---|
| 69 | Propane-2-sulfonic acid (4''-cyano-[1,1';4',1'']terphen-yl-2-yl)-amide | 375 (M − 1) |

EXAMPLE 70

Propane-2-sulfonic acid [2-(propane-2-sulfonylamino)-[1,1',4';1'']terphenyl-2''-yl]-amide Heat in a sealed tube with stirring 2-iodophenylamine (0.5 mmol), 2-(phenyl isopropylsulfamid)boronic acid (0.75 mmol), 2M $Na_2CO_3$ water solution (0.2 mL) and $Pd(PPh_3)_4$ (0.05 mmol) in 4.0 ml of an anhydrous DME to 100° C. for 24 h. Evaporate the organic solvent, prior to the addition of water (10 mL). Extract the mixture with dichloromethane (3×20 mL) and dry the combined organic phases ($Na_2SO_4$). Concentrate to furnish a crude mixture. Purify by flash chromatography (Silica gel-hexane/EtOAc).

Add dropwise DBU drop wise (8.76 mL, 56.92 mmol) to a solution of the resultant amine (14.23 mmol) in dichloromethane (50ml) at 0° C., followed by drop wise addition of isopropylsulfonyl chloride (3.29 mL, 28.46 mmol) and stir the reaction at room temperature for 24 h. Remove solvent under reduce pressure and purify the residue by silica and eluting with EtOAc:hexane 1:4 to EtOAc to provide the title compound (4.93 g, 98%). MS (ES−): 471 (M−1)

EXAMPLE 71

Propane-2-sulfonic acid [4-(3',5'-difluoro-4'-hydroxy-biphenyl-4-yl)-pyridin-3-yl]-amide Dissolve 2,2-Dimethyl-propionic acid 3,5-difluoro-4'-[3-(propane-2-sulfonylamino)-pyridin-4-yl]-biphenyl-4-yl ester in THF (9 ml) and ethanol (1 ml). Add NaOH 2N (10 ml) and heat the mixture to 60° C. for 7 h. Evaporate solvents and add HCl 3N to acidify the mixture. Apply the acidic mixture to 2 g SCX cartridge. Elute the SCX cartridge with methanol (×3) to remove non-basic impurities. Elute the product with 2N ammonia in methanol to afford, after evaporation, 55.2 mg of the title compound as a yellow solid (50% yield). MS (ES−): 403.

EXAMPLE 72

2-Cyano-4'-[3-(propane-2-sulfonylamino)-thiophen-2-yl]-biphenyl-4-carboxylic acid Charge a 10 L double jacketed reactor equipped with mechanical stirring, set under inert atmosphere of argon with [2-(4-bromo-phenyl)-thiophen-3-yl]-carbamic acid tert-butyl ester (800 g, 2.25 mol) and EtOAc (3.2 L). Cool the yellow solution is down to 16.9° C. and add a solution of 5-6N HCl/IPA (1600 mL) in 10 minutes via a dropping funnel between 10° C. and 25° C. Heat the reaction mixture to 50° C. Stir the resulting suspension for 90 minutes at 50° C. Cool the suspension below 10° C. and add 2N NaOH solution (2773 mL) over 25 minutes, maintaining the temperature below 20° C. Add 2N NaOH (450 mL) to reach a pH of 12-13. Separate the two layers by decantation. Re-extract the aqueous phase with EtOAc (500 mL). Dry the combined organic layers over $MgSO_4$ (200 g) and evaporate to dryness to yield 2-(4-Bromo-phenyl)-thiophen-3-ylamine (562.3 g, 2.21 mol) as a beige solid. $^1$H NMR (250 MHz, $CDCl_3$): 3.70(s (broad), 2 H) 6.65(d,1 H, J=5.4 Hz), 7.06(d, 1 H, J=5.2 Hz), 7.32(d, 2 H, J=8.9 Hz), 7.45 (d, 2H, J=8.8 Hz).

Charge a double jacketed 20 L reactor equipped with mechanical stirrer and set under inert atmosphere of argon with 2-(4-Bromo-phenyl)-thiophene-3-ylamine (562 g, 2.21 mol) and $CH_2Cl_2$ (9.435 L). Obtain a clear solution. Add DBU (1.999 L) and cool the mixture to 9.4° C. Add propane-2-sulfonyl chloride (0.616 g) in 20 minutes maintaining the temperature below 25° C. Stir the reaction mixture 22 h at 20° C. After completion of reaction, cool the reaction mixture to 11° C. and add an aqueous solution of satd. aq. $NH_4Cl$ (7.65 L) cooled at 10° C. in 5 minutes. Heat the mixture to 20° C. and separate the aqueous phase. Wash the organic layer with 2N HCl (5.12 L), evaporate to dryness and take the residue into ethyl alcohol (800 g). Heat the mixture until complete dissolution at 70° C. Cool the solution to 41° C. and add water (1384 mL). Stir the suspension overnight at 22° C., filter and wash two times with 254 mL of a 1/1 EtOH/$H_2O$ mixture. Dry the resulting beige solid under vacuum at 26° C. for 4 days to give propane-2-sulfonic acid[2-(4-bromo-phenyl)-thiophene-3-yl]-amide (688 g, 1.9 mol). $^1$H NMR (250 MHz, $CDCl_3$): 1.25(d,6 H, J=6.9 H), 3.16 (hept, 1 H, J=6.9 Hz), 7.28(pseudo s, 2 H), 7.33(d, 2 H, J=8.5 Hz), 7.6(d, 2 H, J=8.5 Hz)

Charge a 10 L double jacketed reactor equipped with a mechanical stirrer, a reflux condenser and set under $N_2$ with propane-2-sulfonic acid[2-(4-bromo-phenyl)-thiophene-3-yl]-amide (688 g, 1.91 mol), DMF (7.74 L), bis-(pinacolato) diboron (533 g, 2.09 mol), "$PdCl_2$dppf (78 g) and potassium acetate (562 g). Heat the resulting mixture to 80° C. for 1 h. Cool the mixture down to 20° C. Quench the mixture with water (8650 mL) and extract with EtOAc (3440 mL). Re-extract the aqueous phase with EtOAc (4587 mL). Combine all the organic layers and evaporate to dryness to give 1420 g of crude material. Purify the crude material filtration on silica gel (7 kg), eluting with n-heptane: EtOAc (6:3) to yield after evaporation to dryness propane-2-sulfonic acid {2-[4-(4,4,5,5-tetramethyl-[1,3,2]dioxaborolan-2-yl)-phenyl]-thiophen-3-yl}-amide as a yellow solid (747 g). $^1$H NMR (250 MHz, $CDCl_3$): 1.19 (d, 6H, J=6.9 Hz), 1.37(s, 12 H), 3.12 (hept, 1 H, J=6.9 Hz) 7.27(d, 1 H, J=5.2 Hz), 7.32 (d,1 H, J=5.2 Hz) 7.43 (d, 1H, J=8.1 Hz), 7.89 (d, 2 H, J=8.1 Hz).

Charge a 10 L double jacketed reactor with a mechanical stirrer and a reflux condenser with 4-hydroxy benzoic acid ethyl ester (967 g, 8.81 mol) and acetic acid (5.8 L). Heat the mixture to 65° C. and add a solution of ICl (1010 g) in acetic acid (1 L) in ½ h. Stir the resulting mixture at 60-62° C. for 16 h. Cool the black solution to 20° C. and transfer on water (5 L) and ice (7.5 kg). Stir the resulting suspension over 1 h at 20° C., filter and wash the cake with water (2 L) and cyclohexane (6 L). Dry the solid under vacuum at 55° C. till constant weight to give 4-hydroxy-3-iodo-benzoic acid ethyl ester (1372.8 g, 4.70 mol). $^{11}$H NMR (250 MHz, $CDCl_3$): 1.38 (t, J=7.1 Hz, 3H), 4.35 (quartet, J=7.1 Hz, 2H), 5.8 (s, 1 H), 7.01 (d, J=8.5 Hz, 1H), 7.95 (dd, J=8.5 Hz, 2.0 Hz, 1H), 8.37 (d, J=2 Hz, 1 H).

Charge a 10 L double jacket reactor, equipped with a mechanical stirrer, a reflux condenser and set under $N_2$ with 4-hydroxy-3-iodo-benzoic acid ethyl ester (1312 g, 4.49 mol), dimethylsulfoxide (3277 mL) and CuCN (442.3 g). Heat the mixture to 105° C. and hold at this temperature for 2.5 h. Cool the brown solution down to 20° C. Add water at 48° C. water (6.5 L) Filter the mixture at 20° C., then wash the cake with water (2 L). Suspend the cake in EtOAc (5 L) and stir during 1 h at 20° C. Filter the suspension on Hyflo Super Cel® (250 g) and rinse with EtOAc (3 L). Decant the filtrates, then evaporate the organic layer to dryness. Take the residue up in n-heptane (10 L). Distill off 2 L of n-heptane, then add $CH_2Cl_2$ (400 mL). Cool the mixture cooled to 27° C., filter and rinse the cake with n-heptane (2 L). Dry 48 h at 55° C. under pressure to give 4-hydroxy-3-cyano-benzoic acid ethyl ester. (777.7 g, 4.067 mol). $^1$H NMR (250 MHz, DMSOd): 1.32 (t, j=7.1 Hz, 3H), 4.3 (q, j=7.1 Hz, 2H), 7.13(d, j=8.8 Hz, 1H), 8.07(dxd, j=8.8 Hz, 2.2 Hz, 1H), 8.16 (d, j=2.2 Hz), 12.11(s (broad), 1H).

Charge a 20 L double jacketed reactor equipped with mechanical stirrer, set under inert atmosphere of argon with 4-hydroxy-3-cyano-benzoic acid ethyl ester (720 g, 3.766 mol) and $CH_2Cl_2$. Cool the brown suspension to 5° C. and add $Et_3N$ (792 mL) resulting in a brown solution. Add DMAP (69.1 g) at 5° C. Add Trifluoromethanesulfonic anhydride (950 mL) over 25 min while maintaining the temperature between 2° C. and 23° C. Stir for ½ h at 20° C., then add 1N HCl (8 L). Separate the aqueous and organic layers and wash the organic layer with a 10% aqueous $NaHCO_3$ solution (8 L). Treat the organic layer with 300 g $MgSO_4$ and evaporate to dryness to give 3-cyano-4-trifluoromethoxycarbonyloxy-benzoic acid ethyl ester as a brown solid (1218.7 g, 3.77 mol). $^1$H NMR (250 MHz, $CDCl_3$): 1.52 (t, J=7.1 Hz, 3H), 4.55(q, J=7.1 Hz, 2H), 7.69 (d, J=8.8 Hz, 1H), 8.49(dxd, J=8.8 Hz, J=2.2 Hz, 1H), 8.55 (d, J=2.2 Hz, 1H)

Charge a 10 L double jacketed reactor equipped with mechanical stirrer, a reflux condenser and set under $N_2$ with palladium acetate (41 g) and DME (6.29 L). Add triphenylphosphine (190 g) to the orange solution. A yellow precipitate forms. Stir the mixture for 15 minutes at 20° C. Add propane-2-sulfonic acid {2-[4-(4,4,5,5-tetramethyl-[1,3,2] dioxaborolan-2-yl)-phenyl]-thiophen-3-yl}-amide (747 g; 1.83 mol), 3-cyano-4-trifluoromethoxycarbonyloxy-benzoic acid ethyl ester (822 g, 2.54 mol), ethyl alcohol (3.14 L) and 2N aqueous $Na_2CO_3$ (1.82 L) and heat the mixture is heated to reflux. After 1 h, further addition of 3-cyano-4-trifluoromethoxycarbonyloxy-benzoic acid ethyl ester may be necessary to complete consumption of propane-2-sulfonic acid {2-[4-(4,4,5,5-tetramethyl-[1,3,2]dioxaborolan-2-yl)-phenyl]-thiophen-3-yl}-amide. Cool the dark brown mixture to 20° C., quench with $H_2O$ (9250 mL) and extract with $CH_2Cl_2$ (9250 mL). Wash the separated organic layer two times with 7 L of 1N aqueous $Na_2CO_3$ and evaporate to dryness to give 1126 g of oil. Dissolve the crude oil into ethyl alcohol (4.1 L) and transfer to a 10 L reactor vessel under inert atmosphere. Add $H_2O$ (6.6 L) and 9N NaOH solution (1.9 L) at 20° C. Heat the brown mixture to 50° C. and stir during 1 h. Cool the mixture and evaporate under reduced pressure in a 20 L rotavapor flask. Distill off 2 L of ethanol while adding 37% HCl (1500 mL) slowly to the mixture during the distillation. Control pH and add 200 ml of 37% HCl reach pH 0-1. Continue the distillation until 5 to 6 L of distillate is obtained. Cool the resulting residue down between 10 and 20° C. and add $CH_2Cl_2$ (1332 mL). Stir the mixture over 4 h at 21° C., filter and wash with $H_2O$ (400 mL) and $CH_2Cl_2$ (400 ml). Dry the brown solid under vacuum at 55° C. during 16 h to yield 546.3 g of the title compound. $^1H$ NMR (250 MHz, DMSOd): δ ppm 1.32(t, J=6.6 Hz, 6H) 3.26 (septet, J=6.6 Hz, 1H) 7.32 (d, J=5.4 Hz, 1H) 7.79 (d, J=5.4 Hz, 1H) 7.93 (d, J=8.2 Hz, 1H) 8.01 (d, J=7.9, 1H) 8.04 (d, J=8.2 Hz, 2H) 8.48 (dd, J=8.2 Hz, 2.2 Hz, 1H) 9.5 (s, 1H), 13.79 (s(broad), 1H).

EXAMPLE 74

Propane-2-sulfonic acid {2-[4'-1H-tetrazol-5-yl)-biphenyl-4-yl]-thiophen-3-yl}-amide Heat in a sealed tube with stirring propane-2-sulfonic acid-[2-(4'-cyano-biphenyl-4-yl)-thiophen-3-yl]-amide (0.5 mmol), $Bu_3SnN_3$ (2.0 mmol) to 100° C. for 24 h. If necessary, add toluene or dichloromethane to help complete the reaction. (1.0 mL of dicholormethane added). Evaporate the organic solvent, if added, prior to the addition of water (10 mL). Extract the mixture with dichloromethane (3×20 mL) and dry the combined organic phases ($Na_2SO_4$). Concentrate to furnish a crude mixture. Purification by flash chromatography (Silica gel-$CH_2Cl_2$/Methanol 8:1) yields the title compound. MS (ES-): 424 (M-1).

Prepare the following compounds in a manner analogous to the procedure described in the above example:

| EXAMPLE | COMPOUND | DATA MS (ES-): |
|---|---|---|
| 75 | Propane-2-sulfonic acid {2-[3'-(1H-tetrazol-5-ylmethyl)-biphenyl-4-yl]-thiophen-3-yl}-amide (dichloromethane 1.0 mL) | 438 (M - 1) |
| 76 | Propane-2-sulfonic acid [2-(1H-tetrazol-5-yl)-[1,1';4',1"]terphenyl-2"-yl]-amide (toluene 1.0 mL dichloromethane 1.0 mL) | 418 (M - 1) |
| 77 | Propane-2-sulfonic acid [4"-(1H-tetrazol-5-yl)-[1,1';4',1"]terphenyl-2-yl]-amide (toluene 0.5 mL) | 418 (M - 1). |

EXAMPLE 78

Propane-2-sulfonic acid {2-[3-cyano-4'-(1H-tetrazol-5-yl)-biphenyl-4-yl]-thiophen-3-yl}-amide Add $NaN_3$ (4.5 mmol) and a 1M solution of $SiCl_4$ (1.5 mmol) in DCM to a solution of 2-Cyano-4'-[3-(propane-2-sulfonylamino)-thiophen-2-yl]-biphenyl-4-carboxylic acid amide (1.5 mmol) in acetonitrile (50 mL). Stir 15 h at 70° C. Concentrate to dryness under reduced pressure. Dissolve resultant residue in 20 ml of $NH_4Cl$ and extract with DCM and the aqueous with EtOAc. Concentrate all organic layers to dryness. Purify by HPLC to provide the title compound. MS (ES-):449(M-1).

Prepare the following compounds in a manner analogous to the procedure set forth in the above example:

| EXAMPLE | COMPOUND | DATA MS (ES-): |
|---|---|---|
| 79 | Propane-2-sulfonic acid {2-[2'-(propane-2-sulfonylamino)-4'-(1H-tetrazol-5-yl)-biphenyl-4-yl]-thiophen-3-yl}-amide | 545 (M - 1) |
| 80 | Propane-2-sulfonic acid {2-[4'-cyano-2'-(propane-2-sulfonylamino)-biphenyl-4-yl]-thiophen-3-yl}-amide | 502 (M - 1) |

EXAMPLE 81

2-(Propane-2-sulfonylamino)-4'-[3-(propane-2-sulfonylamino)-thiophen-2-yl]-biphenyl-4-carboxylic acid methylamide Add oxalyl chloride (0.12 mmol) to a suspension of 2-(Propane-2-sulfonylamino)-4'-[3-(propane-2-sulfonylamino)-thiophen-2-yl]-biphenyl-4-carboxylic acid (0.1 mmol) and DMF (0.05 mmol) in dichloromethane at 0° C. Stir 1 h at RT. Concentrate to dryness under reduced pressure. Dissolve resultant residue in 3 ml $CH_2Cl_2$ and add (2.8 mmol) of $MeNH_2$ (2M in THF). Concentrate the reaction to dryness and purify by flash chromatography (Silica gel- eluting with 5%MeOH/$CH_2Cl_2$). Concentrate the desired fractions to provide the title compound. MS (ES-): 534(M-1).

Prepare the following amides in a manner substantially analogous to the procedure set forth in the above example:

| EXAMPLE | COMPOUND | DATA MS (ES-): |
|---|---|---|
| 82 | 2-Cyano-4'-[3-(propane-2-sulfonylamino)-thiophen-2-yl]-biphenyl-4-carboxylic acid amide | 424 (M - 1). |
| 83 | 2-(Propane-2-sulfonylamino)-4'-[3-(propane-2-sulfonylamino)-thiophen-2-yl]-biphenyl-4-carboxylic acid amide | 520 (M - 1) |

EXAMPLE 84

2-Cyano-4'-[3-(propane-2-sulfonylamino)-thiophen-2-yl]-biphenyl-4-carboxylic acid methylamide Add thionyl chloride (0.2 mmol) to a suspension of 2-Cyano-4'-[3-(propane-2-sulfonylamino)-thiophen-2-yl]-biphenyl-4-carboxylic acid (0.1 mmol) in dichloromethane at RT. Stir mixture for 1 h at 50° C. and concentrate to dryness under reduced pressure. Add to the resultant residue 0.5 mmol $MeNH_2$ (2M in THF). Concentrate the reaction to dryness and purify with flash chromatography (Silica gel-5%MeOH/$CH_2Cl_2$). Concentrate the desired fractions to provide the title compound. MS (ES-):438 (M-1).

EXAMPLE 85

Propane-2-sulfonic acid [2-(5'-amino-3'-fluoro-biphenyl-4-yl)-thiophen-3-yl]-amide Add $SnCl_2.2 H_2O$ (8.5 mmol) to a solution of propane-2-sulfonic acid [2-(3'-fluoro-5'-nitro-biphenyl-4-yl)-thiophen-3-yl]-amide (1.2 mmol) in EtOH (40 mL). Heat the reaction at 70° C. for 30 min and then at room temperature overnight.

Add a saturated solution of NaHCO₃ (pH=11-12) and extract with EtOAc (2×50 mL). Dry over NaSO₄, filter and evaporate to dryness to provide the title compound. MS (ES−): 389 (M−1).

Prepare the following compound in a manner analogous to the procedure set forth in the above example:

| EXAMPLE | COMPOUND | DATA MS (ES−): |
|---|---|---|
| 86 | Propane-2-sulfonic acid [2-(3'-amino-4'-fluoro-biphenyl-4-yl)-thiophen-3-yl]-amide | 389 (M − 1) |

EXAMPLE 87

Propane-2-sulfonic acid [2-(4'-methylaminomethyl-biphenyl-4-yl)-thiophen-3-yl]-amide Mix propane-2-sulfonic acid [2-(4'-formyl-biphenyl-4-yl)-thiophen-3-yl]-amide (0.16 mmol) in 1,2-dichloroethane (2 ml) and add methylamine 2N in THF (0.16 ml, 0.32 mmol) at room temperature. Stir the resulting solution for 5 min before adding Na(OAc)₃BH (0.32 mmol). Stir the mixture at room temperature for 16 h. Analyze by LC/MS for final product. Add saturated NaHCO₃ aqueous solution and dichloromethane and filter the mixture through hydrophobic filter. Evaporate the filtrate and apply the residue to SCX cartridge, elute with MeOH/DCM to remove non-basic materials, followed by 2N NH₃ in MeOH to give a crude product. Purify by flash chromatography (Silica gel-Dichloromethane/Methanol 7:1)to yield the title compound. MS (ES−): 399(M−1).

EXAMPLE 88

Propane-2-sulfonic acid (2-{2',2'-bis-[(propane-2-sulfonylamino)-methyl]-biphenyl-4-yl}-thiophen-3-yl)-amide, and propane-2-sulfonic acid (2-{2'-[(propane-2-sulfonylamino)-methyl]-biphenyl-4-yl}-thiophen-3-yl)-amide Slowly add a solution of BH₃Me₂S (0.05 ml, 0.5 mmol, 2 eq.) in 1.5 mL of THF to a solution of 95 mg of propane-2-sulfonic acid [2-(2"-cyano-biphenyl-4-yl)-thiophen-3-yl]-amide (0.25 mmol, 1 eq.) in 1.5 mL of THF. Heat the mixture to reflux for 2 h and then cool to RT. Decompose the excess borane by adding 0.1 mL of methanol and then a mixture of 0.1 mL of methanol and 0.03 mL of hydrochloride solution. Reflux the reaction for another 15 min. Remove the solvent and add 6 mL of ethanol to remove the thioether. Suspend the solid in 20 mL of saturated saturated aq. sodium chloride and basify with ammonia. Extract with EtOAc(3×10), dry, and remove solvent. Purification by flash chromatography (Silica gel-hexane/EtOAc) affords propane-2-sulfonic acid [2-(2'-aminomethyl-biphenyl-4-yl)-thiophen-3-yl]-amide (100 mg, 62%). MS (m/e): 387.2(M+1).

Add 1,8-diazabicyclo [5.4.0] undec-7-ene (DBU) drop wise (85 mg, 0.6 mmol) to a suspension of propane-2-sulfonic acid [2-(2'-aminomethyl-biphenyl-4-yl)-thiophen-3-yl]-amide (57 mg, 0.15 mmol) in dichloromethane (2 ml) at 0° C., followed by drop wise addition of isopropylsulfonyl chloride (42 mg, 0.3 mmol) and stir the reaction at room temperature overnight. Remove solvent under reduce pressure. Purify with flash chromatography (Silica gel-hexane/EtOAc). Concentrate the desired fractions to provide propane-2-sulfonic acid (2-{2'-[(propane-2-sulfonylamino)-methyl]-biphenyl-4-yl}-thiophen-3-yl)-amide. MS (m/e): 491.1(M−1), propane-2-sulfonic acid (2-{2',2'-bis-[(propane-2-sulfonylamino)-methyl]-biphenyl-4-yl}-thiophen-3-yl)-amide. MS (m/e): 510.2(M−1).

EXAMPLE 89

4'-[5-Chloro-3-(propane-2-sulfonylamino)-thiophen-2-yl]-2-cyano-biphenyl-4-carboxylic acid Dissolve 2-cyano-4'-[3-(propane-2-sulfonylamino)-thiophen-2-yl]-biphenyl-4-carboxylic acid (0.021 g) in dry tetrahydrofuran (0.5 mL) at 0° C. and add N-chlorosuccinimide (0.007 g). Allow the reaction mixture to reach RT and stir for 72 h. Add diethyl ether, concentrate in vacuo and purify by Strata® silica gel cartridges, eluting with dichloromethane-methanol gradient. Purify by reverse phase HPLC to give 0.004 g of the title compound as a white solid. MS (ES−) (m/z): 459 (M−1).

EXAMPLE 90

Propane-2-sulfonic acid [2-(2'-cyano-4'-methanesulfonylaminocarbonyl-biphenyl-4-yl)-thiophen-3-yl]-amide Add methanesulfonamide (0.28 mmol), EDCI (0.28 mmol) and DMAP (0.28 mmol) to a solution of 2-Cyano-4'-[3-(propane-2-sulfonylamino)-thiophen-2-yl]-biphenyl-4-carboxylic acid (0.235 mmol) in DCM. Stir 8 h at RT. Add 1N HCl and extract with DCM. Concentrate all organic layers to dryness. Purify by HPLC to provide the title compound. MS (ES−): 502 (M−1)

EXAMPLE 91

5-Methylsulfanyl-3"-(propane-2-sulfonylamino)-[1,1';4',1"]teriphenyl-2-carboxylic acid Mix 4-Methylsulfanyl-2-trifluoromethanesulfonyloxy-benzoic acid methyl ester (1.216 g, 3.682 mmol), 4,4,5,5-Tetramethyl-1,3,2-dioxaborolane (0.85 ml, 5.682 ), Et₃N (1.55 ml, 11.121 mmol) and acetonitrile (40 ml) then heat to reflux for 16 hours. Dilute the reaction with EtOAc and wash with water. Concentrate under reduced pressure. Next add propane-2-sulfonic acid (4'-bromo-biphenyl-2-yl)-amide (0.532 g, 1.502 mmol) 2N Na₂CO₃ (7 ml, 14 mmol), 1,4-dioxane (35 ml) and tetrakis triphenyl phosphine palladium (0.177 g, 0.153 mmol). Heat to 80° C. for 16 hours. Cool the reaction, dilute with EtOAc, and wash with H₂O, followed by saturated aqueous sodium chloride. Dry with Na₂SO₄ and concentrate under reduced pressure. Purify the reaction by flash chromatography (Silica gel-toluene then up to 20% EtOAc/Hexane) to give 5-Methylsulfanyl-3"-(propane-2-sulfonylamino)-[1,1';4',1"]terphenyl-2-carboxylic acid methyl ester (0.431 g, 63%). MS (m/e): 456(M+1).

Mix the resultant ester (0.120 g, 0.263 mmol), 1N NaOH (1 ml, 1 mmol) and MeOH (1 ml) heat flask to reflux for 1 hour and stir for 16 hours. Next add 0.2N HCl (5 ml, 1 mmol) and cool in- ice bath. Filter the solid. Obtain 5-Methylsulfanyl-3"-(propane-2-sulfonylamino)-[1,1';4',1"]terphenyl-2-carboxylic acid (0.090 g, 77%). MS (m/e): 442(M+1).

EXAMPLE 92

6-Cyano-5-methylsulfanyl-3"-(propane-2-sulfonylamino)-[1,1';4',1"]terphenyl-2-carboxylic acid Mix 2"-Amino-6-cyano-5-methylsulfanyl-[1,1';4',1"]terphenyl-2-carboxylic acid (0.195 g, 0.521 mmol) and dichloromethane (6 ml) then cool to 0° C. Next add DBU (0.33 ml, 2.162 mmol), and $ClSO_2CH(CH_3)_2$ (0.13 ml, 1.128 mmol) drop wise to the solution and stir for 16 hours. If TLC shows remaining SM, add DBU (0.3 ml) and $ClSO_2CH(CH_3)_2$ (0.1 ml) and stir for 16 hours. Dilute the reaction with $CH_2Cl_2$ (50 ml) and wash with $H_2O$, satd aq. sodium chloride, dry with $Na_2SO_4$, and concentrate under reduced pressure. Analyze by TLC and if reaction has remaining SM add MeOH (2 ml) and 1N NaOH (1 ml, 1 mmol). Heat to reflux for 6 hours. Add 1N HCL (1 ml, 1 mmol) and extract into dichloromethane. Purify the reaction by flash chromatography (Silica gel -dichloromethane then up to 10% MeOH/dichloromethane), to give 6-Cyano-5-methylsulfanyl-3"-propane-2-sulfonylamino)-[1,1';4',1"]terphenyl-2-carboxylic acid (0.008 g). MS (m/e): 467(M+1).

EXAMPLE 93

Propane-2-sulfonic acid (2-biphenyl-4-yl-2H-pyrazol-3-yl)-amide

Add cesium fluoride (0.221 g, 1.45 mmol) and dichloro[1,1'bis(diphenylphosphino)ferrocene]palladium (II) dichloromethane adduct (0.024 g, 0.029 mmol) to a mixture of propane-2-sulfonic acid [2-(4-bromo-phenyl)-2H-pyrazol-3-yl]-amide (0.100 g, 0.290 mmol) and 2-cyanophenylboronic acid (0.043 g, 0.290 mmol) in anhydrous 1,2-dimethoxyethane (5.0 mL). Deoxygenate the mixture three times, immerse into a pre-heated (85° C.) oil bath, and stir for 30 h. Dilute the mixture with water and dichloromethane, filter through Celite®, and wash through with dichloromethane. Concentrate the mixture, re-dissolve in dichloromethane, adsorb onto silica gel, and subject to silica gel flash column chromatography (12 g column, eluting with a gradient of 0-10% methanol/dichloromethane for 40 min., followed by (20% 2.0M NH3 in methanol/dichloromethane) to yield the title product as a light brown solid (0.036 g, 34%): mass spectrum (m/e): 367.0 (M+1), 365.0 (M−1).

EXAMPLE 94

Propane-2-sulfonic acid (2-biphenyl-4-yl-2H-pyrazol-3-yl)-amide

Add cesium fluoride (0.221 g, 1.45 mmol) and dichloro[1,1'bis(diphenylphosphino)ferrocene]palladium (II) dichloromethane adduct (0.024 g, 0.029 mmol) to a mixture of propane-2-sulfonic acid [2-(4-bromo-phenyl)-2H-pyrazol-3-yl]-amide (0.100 g, 0.290 mmol) and 2-cyanophenylboronic acid (0.043 g, 0.290 mmol) in anhydrous 1,2-dimethoxyethane (5.0 mL). Deoxygenate the mixture thrice, immerse into a pre-heated (85° C.) oil bath, and stir for 30h. Dilute the mixture with water and dichloromethane, filter through Celite®, and wash through with dichloromethane. Concentrate the mixture, re-dissolve in dichloromethane, adsorb onto silica gel, and subject to silica gel flash column chromatography (12 g column, eluting with a gradient of 0-10% methanol/dichloromethane for 40 min., followed by (20% 2.0M $NH_3$ in methanol/dichloromethane) to yield the title product as a light brown solid (0.036 g, 34%): mass spectrum (m/e): 367.0 (M+1), 365.0 (M−1).

General Procedure for the Preparation of Salts and Crystals

A master plate is prepared with 250 μL of the free acid of the subject compound in methanol (0.1 M) added to all wells set in a 96 well format. An array of bases is dispensed to each well in one and two molar equivalents. The solvents are evaporated from all 96 wells using a Genevac Series II evaporator leaving solid residue in the master plate. An array of solvents is dispensed to each one of these wells through a cap mat and then heated to 55° C. with stirring and allowed to equilibrate for 60-90 minutes at about 55° C. Each sample is then filtered hot and transferred to corresponding wells in an evaporation plate, a precipitation plate, and a cooling plate. The evaporation plate is prepared by transferring 200 μL of the filtrate from the master plate using 55° C. heated syringes to the open well titer plate and is then allowed to evaporate to dryness over night at room temperature and ambient humidity. The precipitation plate is prepared by adding 100 μL of the filtrate from the master plate using 55° C. heated syringes to capped 96 well titer plate where each well contains an antisolvent of 200 μL of heptane or 2-propanol. After equilibrating for a period of nine hours at room temperature, the excess solution is wicked away using pre-cut Whatman filter paper. The cooling plate is prepared by transferring 200 μL of the filtrate from the master plate to individual wells using 55° C. heated syringes in a capped titer plate, and cooling exponentially from 55 to 10° C. over a period of 8 hours. Photomicrographs are collected on the material at the bottom of each well in the 96 well plates using a Zeiss Axiovert 200M inverted incident-light microscope with a 2.5× objective. If the material is crystalline, it exhibits birefringence that is displayed as white against a dark background. Amorphous solids appear dark or as opaque droplets or rings.

The ability of compounds of Formula I to potentiate glutamate receptor-mediated response can be determined by one of ordinary skill in the art. For example, see U.S. Pat. No. 6,303,816. In particular, the following test may be utilized:

HEK293 cells stably expressing human iGluR4(obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg−1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis(oxyethylene-nitrilo)tetraacetic acid), pH=7.2 with CsOH, 295 mOsm kg−1. With these solutions, recording pipettes have a resistance of 2-3 MΩ. Using the whole-cell voltage clamp technique (Hamill et al. (1981) Pflügers Arch., 391: 85-100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM or less, they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 µM cyclothiazide is determined by its inclusion in both the bathing solution and the glutamate-containing solution. In this manner, the efficacy of the test compound relative to that of cyclothiazide can be determined. The exemplified compounds were tested essentially as described above and were found to have $EC_{50}$ values less than or equal to 3.0 µM. The following compounds were tested essentially as described above and were found to have the following activity:

| EXAMPLE | $EC_{50}$ (µM) |
|---------|----------------|
| 56 | 0.151 |
| 11 | 0.720 |
| 51 | 2.463 |
| 76 | 0.445 |
| 72 | 0.188 |
| 46 | 0.977 |

In addition, certain behavioral despair animal models, which can be practiced by one of ordinary skill in the art to evaluate compounds of the present invention, are predictive of antidepressant activity in man, such as the Forced Swim Test and the Tail Suspension Test. For example, see "Experimental Approaches to Anxiety and Depression", Edited by J. M. Elliott, et al., (1992), John Wiley & Sons Ltd., Chapter 5, *Behavioural Models of Depression*, Porsolt and Lenegre, pages 73-85.

The pharmaceutical compositions of the present invention are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 0.1 mg to about 300 mg, preferably about 0.1 mg to about 100 mg, and most preferably about 1.0 to about 100 mg of compound of Formula I. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

As used herein the term "patient" refers to a mammal, such as a mouse, guinea pig, rat, dog or human. It is understood that the preferred patient is a human.

As used herein, the terms "treating" or "to treat" or "treatment" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of Formula I which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I can be administered by a variety of routes including oral, rectal, transdermal, subcutaneous, intravenous, intramuscular, bucal or intranasal routes. Alternatively, the compound of Formula I may be administered by continuous infusion. A typical daily dose will contain from about 0.005 mg/kg to about 10 mg/kg of the compound of Formula I. Preferably, daily doses will be about 0.005 mg/kg to about 5 mg/kg, more preferably from about 0.005 mg/kg to about 2 mg/kg.

The dosages of the drugs used in the combinations set forth herein, must also, in the final analysis, be set by the physician in charge of the case, using knowledge of the drugs, the properties of the drugs in combination as determined in clinical trials, and the characteristics of the patient, including diseases other than that for which the physician is treating the patient.

The inert ingredients and manner of formulation of the adjunctive pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compounds, however, is best defined as the effective amount, that is, the amount of each compound which provides the desired dose to the patient in need of such treatment.

For example, a formulation may include 1% carboxymethylcellulose sodium, 0.25% polysorbate 80 and 0.05% Dow Corning Antifoam 1510-US in purified water) through the oral route. For the IV administration, a composition of 5% pharmasolve, 0.4% 1N NaOH, 94.6% Dextrose 5% in water may be used.

We claim:
1. A compound of Formula I:

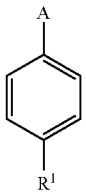

where:
A is selected from the group consisting of

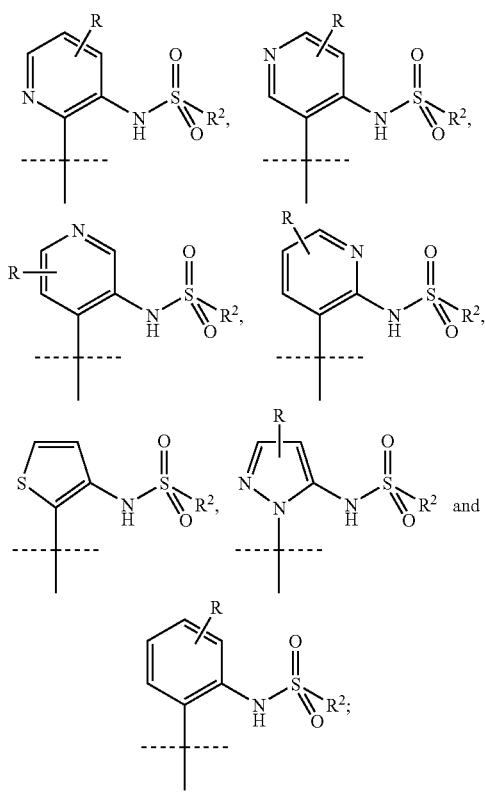

R is H, halo, —COOH, or —CH$_2$COOH;
R$_1$ is phenyl optionally substituted with a first substituent selected from the group consisting of halo, cyano, C$_1$-C$_4$acyl, —COOH, —NHR$^3$, C$_1$-C$_2$ alkyl substituted with —NHCH$_3$, —N(SO$_2$(C$_1$-C$_3$alkyl))$_2$, —COOH, —CONH$_2$, cyano, hydroxy, or tetrazol-5-yl, —OCH$_2$COOH, —SCH$_2$COOH, —C(O)CH$_2$CH$_2$COOH, —SO$_2$NH$_2$, tetrazol-5-yl, and 1,2,4-triazol-1-yl; optionally further substituted with a second substituent selected from the group consisting of: halo, trifluoromethyl, cyano, nitro, C$_1$-C$_4$alkoxy, hydroxy, C$_1$-C$_4$alkyl, C$_1$-C$_4$alkylthio, —NHCH$_2$CN, —OCH$_2$CN, —NHSO$_2$CH(CH$_3$)$_2$, and —C(O)NHR$_4$; optionally further substituted with a third substituent selected from the group consisting of halo and cyano; optionally further substituted with a fourth substituent selected from the group consisting of halo;
R$^2$ is C$_1$-C$_4$ alkyl or dimethylamino;
R$^3$ is —SO$_2$(C$_1$-C$_3$ alkyl), C$_1$-C$_4$ acyl, C$_1$-C$_4$ alkyl, or hydrogen;
R$^4$ is hydrogen, C$_1$-C$_4$ alkyl, or —SO$_2$(C$_1$-C$_4$ alkyl); or a pharmaceutically acceptable salt thereof, provided that when A is

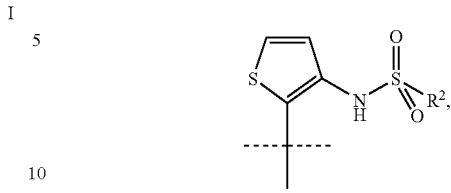

and R$^2$ is isopropyl, then R$^1$ is not 2-ethoxy-4-carboxyphenyl.

2. A compound of claim 1 where A is

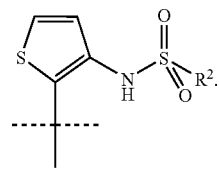

3. A compound of claim 1 where R$^2$ is isopropyl.
4. The compound 2-Cyano-4'-[3-(propane-2-sulfonylamino)-thiophen-2-yl]-biphenyl-4-carboxylic acid, or a pharmaceutically acceptable salt thereof.
5. A pharmaceutical formulation comprising a compound of Formula I in combination with a pharmaceutically acceptable carrier, diluent or excipient.
6. A pharmaceutical formulation according to claim 5 wherein the compound of Formula I is 2-Cyano-4'-[3-(propane-2-sulfonylamino)-thiophen-2-yl]-biphenyl-4-carboxylic acid, or a pharmaceutically acceptable salt thereof.
7. A compound of Formula II:

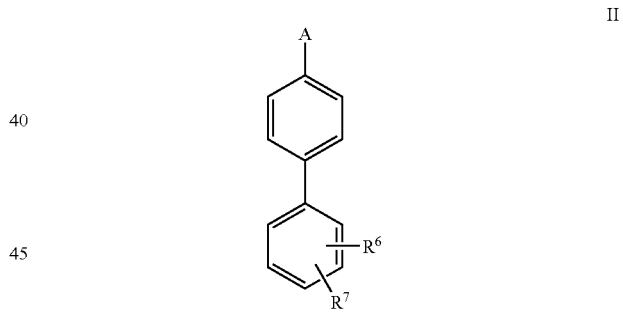

where:
A is selected from to group consisting of

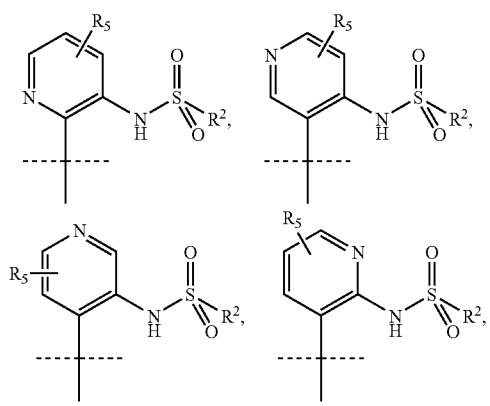

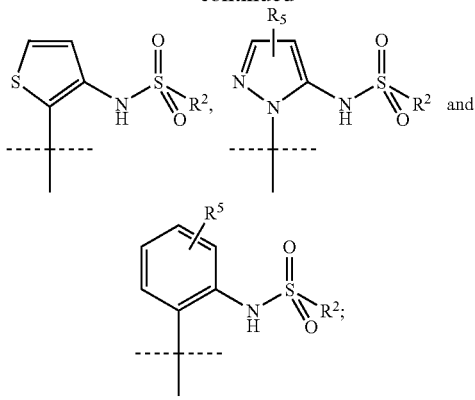

R² is C₁-C₄ alkyl or dimethylamino;

R⁵ is H, halo, —COOR⁸, or —CH₂COOR⁵;

R⁶ is H, cyano, C₁-C₄ alkoxy, halo, hydroxy, trifluoromethyl, or methylthio;

R⁷ is —COOR⁹, —C(O)CH₂CH₂COOR⁹, —OCH₂COOR⁹, —SCH₂COOR⁹, or C₁-C₂ alkyl substituted with —COOR⁹;

R⁸ and R⁹ are each independently selected from to group consisting of hydrogen and C₁-C₄ alkyl provided that at least one of R⁸ and R⁹ is other than hydrogen; or a base addition salt thereof.

* * * * *